(12) United States Patent
Wegrzyn, III et al.

(10) Patent No.: US 12,097,313 B2
(45) Date of Patent: Sep. 24, 2024

(54) PERITONEAL DIALYSIS SYSTEM INCLUDING MANIFOLD ASSEMBLY AND PERISTALTIC PUMP

(71) Applicants: BAXTER INTERNATIONAL INC., Deerfield, IL (US); BAXTER HEALTHCARE SA, Glattpark (CH)

(72) Inventors: Thomas John Wegrzyn, III, Evanston, IL (US); Thomas Idstein, Grayslake, IL (US); Edward Davis, Johnsburg, IL (US); Shawn Jones, Cary, IL (US); Serhan Acikgoz, Des Plaines, IL (US); Rongsheng Lin, Buffalo Grove, IL (US); Bahram Notghi, Valley Village, CA (US); James Ascenzo, Glen Ellyn, IL (US); Jorge Del Castillo, Des Plaines, IL (US)

(73) Assignees: BAXTER INTERNATIONAL INC., Deerfield, IL (US); BAXTER HEALTHCARE SA, Glattpark (CH)

( * ) Notice: Subject to any disclaimer, the term of this patent is extended or adjusted under 35 U.S.C. 154(b) by 0 days.

(21) Appl. No.: 18/266,538

(22) PCT Filed: Dec. 9, 2021

(86) PCT No.: PCT/US2021/062657
§ 371 (c)(1),
(2) Date: Jun. 9, 2023

(87) PCT Pub. No.: WO2022/125801
PCT Pub. Date: Jun. 16, 2022

(65) Prior Publication Data
US 2023/0390469 A1 Dec. 7, 2023

Related U.S. Application Data

(60) Provisional application No. 63/123,796, filed on Dec. 10, 2020.

(51) Int. Cl.
*A61M 1/28* (2006.01)
*A61M 1/14* (2006.01)

(52) U.S. Cl.
CPC .............. *A61M 1/282* (2014.02); *A61M 1/15* (2022.05); *A61M 1/152* (2022.05);
(Continued)

(58) Field of Classification Search
CPC .......... A61M 1/14; A61M 1/15; A61M 1/152; A61M 1/1524; A61M 1/155; A61M 1/156;
(Continued)

(56) References Cited

U.S. PATENT DOCUMENTS

2003/0136189 A1 7/2003 Lauman et al.
2005/0209563 A1 9/2005 Hopping et al.
(Continued)

FOREIGN PATENT DOCUMENTS

WO 2015168280 11/2015

OTHER PUBLICATIONS

International Search Report—PCT/US2021/062657 mailing date Mar. 10, 2022—4 pages.
(Continued)

*Primary Examiner* — Shefali D Patel
(74) *Attorney, Agent, or Firm* — K&L Gates LLP

(57) ABSTRACT

A peritoneal dialysis ("PD") system includes a cycler including an actuation surface having a peristaltic pump actuator; at least one pair of capacitive sensing plates; a manifold assembly including a rigid manifold having at least one chamber, the rigid manifold configured and arranged to be abutted against the actuation surface for operation, wherein the at least one pair of capacitive sensing plates is positioned to be operable with the at least one chamber; a peristaltic pump tube; and a control unit configured to actuate the
(Continued)

peristaltic pump actuator to pump dialysis fluid to the at least one chamber, receive a signal from the at least one pair of capacitive sensing plates, count a number of revolutions of the peristaltic pump actuator, determine a current volume per revolution for the peristaltic pump actuator, and use the current volume per revolution for a subsequent operation of the peristaltic pump actuator.

9 Claims, 13 Drawing Sheets

(52) U.S. Cl.
CPC .......... *A61M 1/1524* (2022.05); *A61M 1/155* (2022.05); *A61M 1/159* (2022.05); *A61M 1/28* (2013.01); *A61M 2205/12* (2013.01); *A61M 2205/121* (2013.01); *A61M 2205/33* (2013.01); *A61M 2205/3379* (2013.01); *A61M 2205/50* (2013.01); *A61M 2205/75* (2013.01)

(58) Field of Classification Search
CPC .............. A61M 1/1561; A61M 1/1562; A61M 1/1563; A61M 1/15632; A61M 1/159; A61M 1/28; A61M 1/282; A61M 2205/12; A61M 2205/121; A61M 2205/123; A61M 2205/33; A61M 2205/3317; A61M 2205/3327; A61M 2205/3379; A61M 2205/3396; A61M 2205/50; A61M 2205/75; A61M 2210/1017; A61M 1/154; A61M 2205/125; A61M 2205/126; A61M 2205/7536

See application file for complete search history.

(56) References Cited

U.S. PATENT DOCUMENTS

2013/0037142 A1 2/2013 Farrell
2019/0201604 A1 7/2019 Hogard

OTHER PUBLICATIONS

Written Opinion—PCT/US2021/062657 mailing date Mar. 10, 2022—6 pages.
International Preliminary Report on Patentability—PCT/US2021/062657 dated Oct. 17, 2022—7 pages.

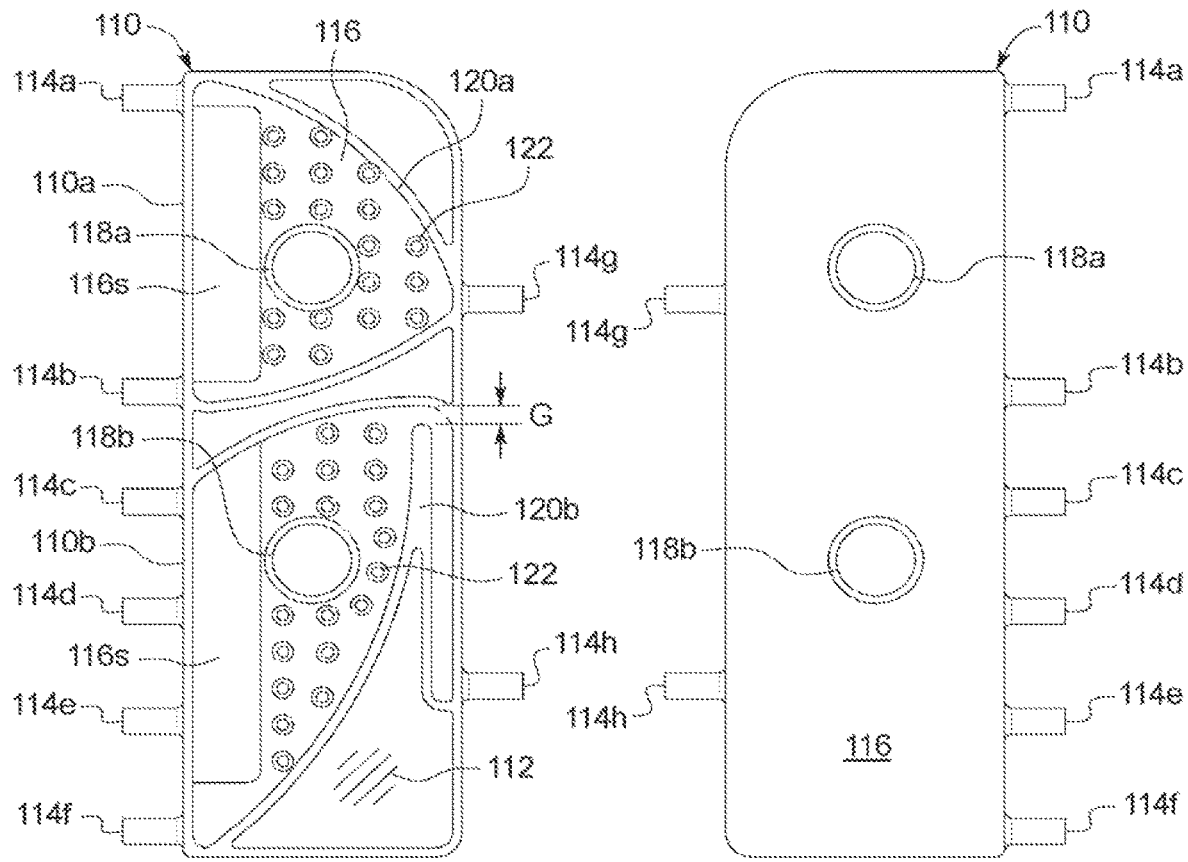
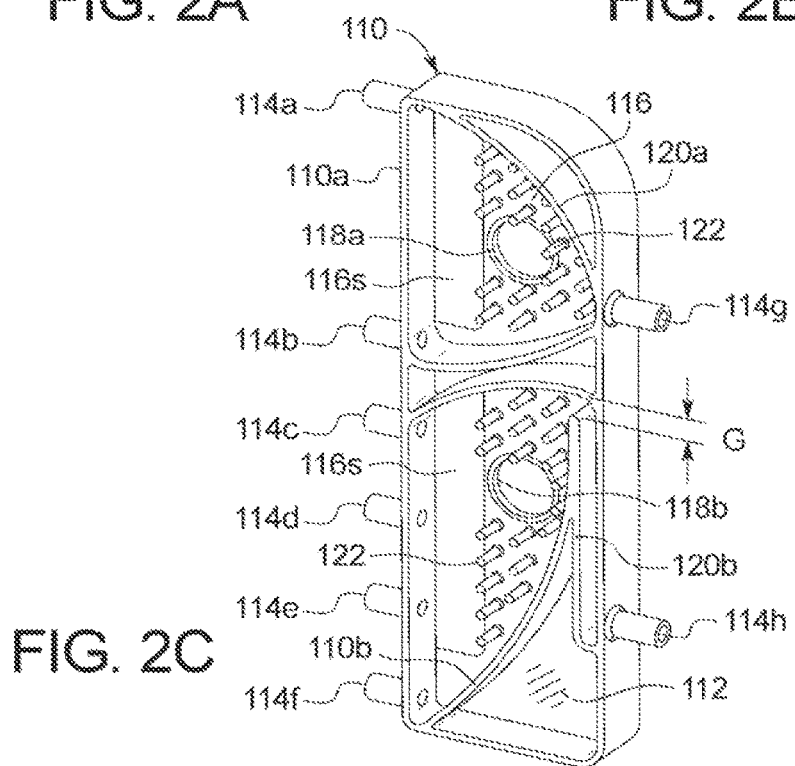

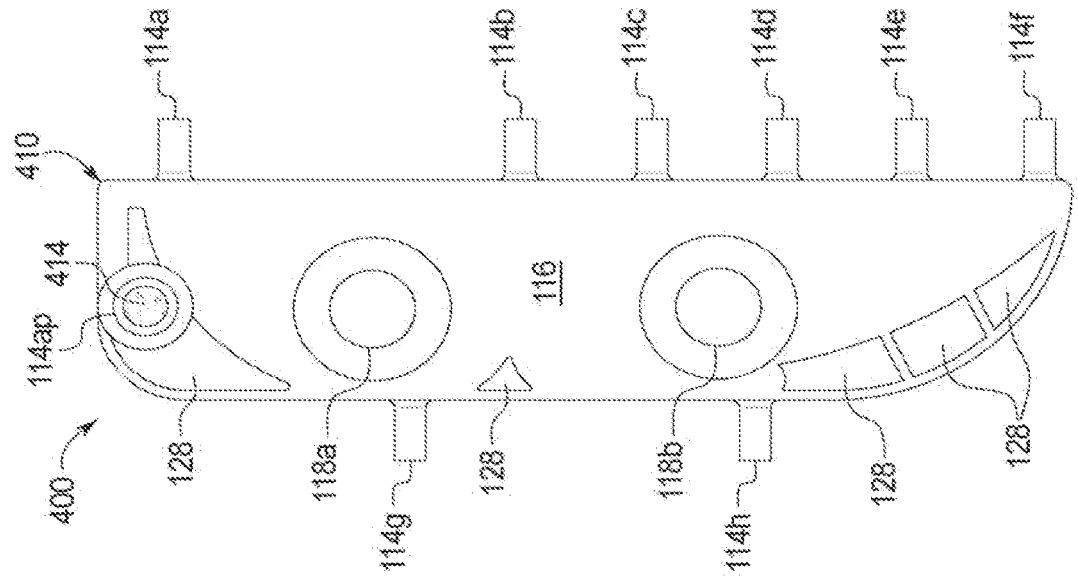
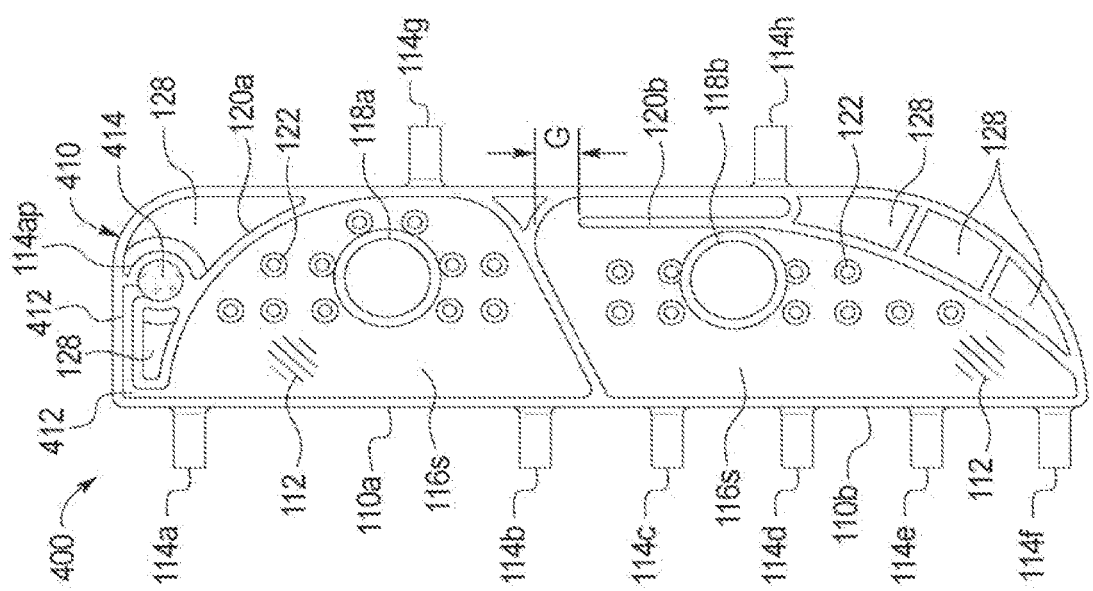

PERITONEAL DIALYSIS SYSTEM INCLUDING MANIFOLD ASSEMBLY AND PERISTALTIC PUMP

PRIORITY CLAIM

The present application is a national phase entry of PCT Patent Application No. PCT/US2021/062657, filed on Dec. 9, 2021, which claims priority to and the benefit of U.S. Provisional Application 63/123,796, filed on Dec. 10, 2020, the entirety of which is are herein incorporated by reference.

BACKGROUND

The present disclosure relates generally to medical fluid treatments and in particular to dialysis fluid treatments.

Due to various causes, a person's renal system can fail. Renal failure produces several physiological derangements. It is no longer possible to balance water and minerals or to excrete daily metabolic load. Toxic end products of metabolism, such as, urea, creatinine, uric acid and others, may accumulate in a patient's blood and tissue.

Reduced kidney function and, above all, kidney failure is treated with dialysis. Dialysis removes waste, toxins and excess water from the body that normal functioning kidneys would otherwise remove. Dialysis treatment for replacement of kidney functions is critical to many people because the treatment is lifesaving.

One type of kidney failure therapy is Hemodialysis ("HD"), which in general uses diffusion to remove waste products from a patient's blood. A diffusive gradient occurs across the semi-permeable dialyzer between the blood and an electrolyte solution called dialysate or dialysis fluid to cause diffusion.

Hemofiltration ("HF") is an alternative renal replacement therapy that relies on a convective transport of toxins from the patient's blood. HF is accomplished by adding substitution or replacement fluid to the extracorporeal circuit during treatment. The substitution fluid and the fluid accumulated by the patient in between treatments is ultrafiltered over the course of the HF treatment, providing a convective transport mechanism that is particularly beneficial in removing middle and large molecules.

Hemodiafiltration ("HDF") is a treatment modality that combines convective and diffusive clearances. HDF uses dialysis fluid flowing through a dialyzer, similar to standard hemodialysis, to provide diffusive clearance. In addition, substitution solution is provided directly to the extracorporeal circuit, providing convective clearance.

Most HD, HF, and HDF treatments occur in centers. A trend towards home hemodialysis ("HHD") exists today in part because HHD can be performed daily, offering therapeutic benefits over in-center hemodialysis treatments, which occur typically bi- or tri-weekly. Studies have shown that more frequent treatments remove more toxins and waste products and render less interdialytic fluid overload than a patient receiving less frequent but perhaps longer treatments. A patient receiving more frequent treatments does not experience as much of a down cycle (swings in fluids and toxins) as does an in-center patient, who has built-up two or three days' worth of toxins prior to a treatment. In certain areas, the closest dialysis center can be many miles from the patient's home, causing door-to-door treatment time to consume a large portion of the day. Treatments in centers close to the patient's home may also consume a large portion of the patient's day. HHD can take place overnight or during the day while the patient relaxes, works or is otherwise productive.

Another type of kidney failure therapy is peritoneal dialysis ("PD"), which infuses a dialysis solution, also called dialysis fluid, into a patient's peritoneal chamber via a catheter. The dialysis fluid is in contact with the peritoneal membrane in the patient's peritoneal chamber. Waste, toxins and excess water pass from the patient's bloodstream, through the capillaries in the peritoneal membrane, and into the dialysis fluid due to diffusion and osmosis, i.e., an osmotic gradient occurs across the membrane. An osmotic agent in the PD dialysis fluid provides the osmotic gradient. Used or spent dialysis fluid is drained from the patient, removing waste, toxins and excess water from the patient. This cycle is repeated, e.g., multiple times.

There are various types of peritoneal dialysis therapies, including continuous ambulatory peritoneal dialysis ("CAPD"), automated peritoneal dialysis ("APD"), tidal flow dialysis and continuous flow peritoneal dialysis ("CFPD"). CAPD is a manual dialysis treatment. Here, the patient manually connects an implanted catheter to a drain to allow used or spent dialysis fluid to drain from the peritoneal chamber. The patient then switches fluid communication so that the patient catheter communicates with a bag of fresh dialysis fluid to infuse the fresh dialysis fluid through the catheter and into the patient. The patient disconnects the catheter from the fresh dialysis fluid bag and allows the dialysis fluid to dwell within the peritoneal chamber, wherein the transfer of waste, toxins and excess water takes place. After a dwell period, the patient repeats the manual dialysis procedure, for example, four times per day. Manual peritoneal dialysis requires a significant amount of time and effort from the patient, leaving ample room for improvement.

Automated peritoneal dialysis ("APD") is similar to CAPD in that the dialysis treatment includes drain, fill and dwell cycles. APD machines, however, perform the cycles automatically, typically while the patient sleeps. APD machines free patients from having to manually perform the treatment cycles and from having to transport supplies during the day. APD machines connect fluidly to an implanted catheter, to a source or bag of fresh dialysis fluid and to a fluid drain. APD machines pump fresh dialysis fluid from a dialysis fluid source, through the catheter and into the patient's peritoneal chamber. APD machines also allow for the dialysis fluid to dwell within the chamber and for the transfer of waste, toxins and excess water to take place. The source may include multiple liters of dialysis fluid including several solution bags.

APD machines pump used or spent dialysate from the patient's peritoneal cavity, though the catheter, and to the drain. As with the manual process, several drain, fill and dwell cycles occur during dialysis. A "last fill" may occur at the end of the APD treatment. The last fill fluid may remain in the peritoneal chamber of the patient until the start of the next treatment, or may be manually emptied at some point during the day.

Known APD systems include a machine or cycler that accepts and actuates a pumping cassette having a hard part and a soft part that is deformable for performing pumping and valving operations. Sealing the fluid disposable cassette with a pneumatic path via a gasket to provide actuation has proven to be a potential field issue, which can delay treatment start time and affect user experience. Pneumatic cassette systems also produce acoustic noise, which may be a source of customer dissatisfaction.

For each of the above reasons, an improved APD machine is needed.

SUMMARY

The present disclosure sets forth a streamlined automated peritoneal dialysis ("APD") cycler and associated system providing a peristaltic pump and a manifold assembly that organizes tubing and performs many functions discussed below. The manifold assembly includes a rigid plastic manifold, which in an embodiment is covered on one side by a plastic sheet for its for ease and cost of manufacturing. In another embodiment, a rigid plastic lid is ultrasonically welded onto the rest of the rigid plastic manifold. The lid may include a slight ridge around its perimeter to aid in the rigidity of the lid.

The rigid plastic manifold is inserted inside of an APD cycler, for example, in between an actuation surface and a door of the APD cycler. The door for example hinges open along a bottom of the cycler housing adjacent to the actuation surface. In one implementation, the rigid plastic manifold of the manifold assembly is mounted so that the plastic sheet of the manifold is located on the surface facing the door and is constrained by the door during operation. The APD cycler includes a peristaltic pump head, which is able to be actuated in two directions by a motor located within the housing of the APD cycler. Pinch valves are provided along the actuation surface of the APD cycler to selectively occlude tubing that extends from the rigid plastic manifold. An air sensor may be located along the actuation surface, e.g., behind where the patient line of the manifold assembly is mounted for operation.

When the rigid plastic manifold is mounted to the actuation surface for operation, ports for receiving tubes extend from both sides of the manifold, e.g., from the right and left sides of the manifold. Ports extending from one side of the manifold (e.g., right side viewing APD cycler from the front) connect sealingly to a peristaltic pumping tube, while the ports from the other side of the manifold (e.g., to the left side viewing APD cycler from the front) are, for example, from top to bottom, a drain port, a first heater line/first dialysis fluid container, a bypass or branch line port, a second dialysis fluid container port, a third dialysis fluid container port and a patient line port. The number of ports provided by each of an upper and a lower chamber are not limited by the number shown and described herein embodiment and may be more or less than shown and described.

The rigid plastic manifold includes a rigid plastic wall that opposes the plastic sheet. The plastic wall abuts up against the actuation surface for operation. One or more apertures, such as circular holes, are formed or provided in the rigid plastic wall. The circular holes are covered with pressure sensing membranes. When the manifold is mounted to the APD cycler for operation, the pressure sensing membranes abut against pressure transducers. The pressure sensors or transducers sense the pressure of fresh and used dialysis fluid entering and leaving the manifold.

A pressure sensing hole and accompanying pressure sensing membrane is provided in the rigid plastic wall of each of the upper and the lower chamber of the rigid plastic manifold. The upper chamber is the primary air collecting chamber, which communicates with the drain port for removing air to drain. The lower chamber communicates fluidly with the lower-most patient line port, which is the most important location to be free of air, wherein air in the patient line naturally tends to buoy upwards away from the patient line and into the lower chamber. In an alternative embodiment, the pressure sensing apertures and corresponding pressure sensing membranes in the rigid plastic wall are provided along an air channel extending away from the upper and/or lower chamber of the manifold.

A drain line and first dialysis fluid container/heater line extend and connect to their respective ports, which communicate fluidly with the upper chamber. A Y-connection or branch line, a second dialysis fluid container line, a third dialysis fluid container line and a patient line extend and connect to their respective ports, which communicate fluidly with the lower chamber. A peristaltic pumping tube extends between and connects to respective ports of the upper and lower chambers. In an embodiment, a peristaltic pump actuator located at the actuation surface of the APD cycler rotates in a first direction to pump fresh, heated dialysis fluid from the upper chamber, through the peristaltic pumping tube, to the lower chamber, and to the patient. The peristaltic pump actuator rotates in the opposite direction to pump used dialysis fluid from the lower chamber, through the peristaltic pumping tube, to the upper chamber, and to drain.

The peristaltic pump actuator also rotates in the opposite direction to pump fresh dialysis fluid from either of the second or third dialysis fluid containers into the lower chamber, through the peristaltic pumping tube, to the upper chamber, and to the previously emptied first dialysis fluid container, which is placed in operable communication with a dialysis fluid heater. By allowing the fresh dialysis fluid from each of the dialysis fluid containers to be heated in the first dialysis fluid container, the disposable dialysis fluid set only has to be loaded once for operation. Additionally, a separate dialysis fluid heating container or bag is not needed.

The first dialysis fluid container is loaded onto dialysis fluid heater for treatment. After the first dialysis fluid container is emptied, the peristaltic pump actuator reverses and pulls fluid from the second dialysis fluid container and pushes same into the first dialysis fluid container for heating. The same procedure is performed for the third dialysis fluid supply container when the second dialysis fluid supply container is emptied. If the dialysis fluid from the second (or third) container is different than that of the first container, the Y-connection or branch line is used to enable the remaining fluid from the first dialysis fluid supply container to be pulled by the peristaltic pump actuator into the lower chamber and then pushed into the upper chamber and out to drain before the differently formulated fluid of the second (or third) dialysis fluid container is delivered to the first dialysis fluid container for heating.

In one embodiment, each of the upper and lower chambers of the manifold is provided with a plurality of pegs extending inwardly from the rigid plastic wall, which prevent the flexible plastic sheet from collapsing under negative pressure. If the flexible sheet is instead replaced with a rigid plastic lid then the pegs are not needed. A certain portion of the rigid plastic wall for each of the upper and lower chambers is not provided with pegs and serves as a capacitive sensing area for the respective upper or lower chamber. Each of the capacitive sensing areas of the rigid plastic wall during operation presses up against a capacitive sensing plate or electrode located along the actuation surface of the APD cycler. The door of the APD cycler is provided with a matching capacitive sensing plate or electrode for each chamber, which each directly oppose the capacitive sensing plates placed along the actuation surface. The matching upper and lower sets of capacitive sensing plates or electrodes form upper and lower capacitive sensors. The capacitive sensors, one for each chamber, detect an amount of air in the respective chamber. If too much air accumulates, the APD cycler stops its current routine and pushes the air to drain in a manner discussed herein.

In addition to the detection of air, the APD system of the present disclosure uses capacitive level sensing to calibrate the peristaltic pump actuator, which is performed in one embodiment when enough air builds in the upper chamber that an air purge to drain needs to be performed. Here, prior to the purge, the peristaltic pump actuator is rotated in a direction to so as to pull fluid from the lower chamber into the upper chamber of the rigid plastic manifold. The upper capacitive sensor detects how much fluid accumulates in the upper chamber over a known amount of peristatic pump strokes or revolutions, so that the current volume/stroke of the peristaltic pump in the current direction may be calculated and used going forward when rotating the peristaltic pump actuator in that same direction, e.g., during patient draining from the lower chamber to the upper chamber. The lower capacitive sensor may be used additionally (for confirmation) or alternatively to detect how much fluid leaves the lower chamber over the known amount of peristatic pump strokes or revolutions, for the calculated volume/stroke of the peristaltic pump in the current direction.

Likewise, prior to the purge, the peristaltic pump actuator is rotated in the opposite direction to push fluid from the upper chamber into the lower chamber of the rigid plastic manifold. The upper capacitive sensor detects how much fluid leaves the upper chamber over the known amount of peristaltic pump strokes or revolutions, so that the volume/stroke of the peristaltic pump in the opposite direction may be calculated and used going forward when rotating the peristaltic pump actuator in that same opposite direction, e.g., for patient filling. The lower capacitive sensor may be used in addition (for confirmation) or alternatively to detect how much fluid accumulates in the lower chamber over a known amount of peristaltic pump strokes or revolutions for the calculated volume/stroke of the peristaltic pump in the opposite direction.

In one embodiment, the upper capacitive sensor is used primarily for calibrating the peristaltic pump stroke volume. The lower capacitive sensor is used mainly for air management, but may be used for confirmation of the pump stroke volume calibration if needed. This configuration assumes however that air management is able to be handled in the lower chamber, which is likely in most instances. It should be appreciated however that if unwanted air from treatment does migrate into the upper chamber, the upper capacitive sensor will detect such air and be used here for air management, e.g., output to a control unit to take corrective action.

In an alternative embodiment, the APD system of the present disclosure uses a three chamber rigid plastic manifold. The three chamber rigid plastic manifold may begin with the two chamber manifold just described, including all of its structure, functionality and alternatives. Additionally, a third chamber is located, e.g., molded, on top of the former upper chamber, making it a middle chamber in the three chamber manifold. One or more aperture may be formed between the middle and upper chamber, however, it is contemplated that fluid does not flow from the middle chamber to the upper, third chamber. Instead, the upper chamber is provided to supply air to the middle chamber during a calibration sequence. It is contemplated to either move a pressure sensing hole and accompanying pressure sensing membrane from the upper chamber of the two chamber manifold to the upper chamber of the three chamber manifold or to add a pressure sensing hole and accompanying pressure sensing membrane to the upper chamber of the three chamber manifold.

In an embodiment, at least one of the parallel plate capacitance sensors are provided again for the three chamber manifold, here with the middle chamber and possibly the lower chamber. The added upper chamber is not intended to hold fluid and does not operate with capacitive sensing plates or electrodes accordingly in one embodiment.

The pumping operation of the alternative three chamber manifold is the same in one embodiment as that for the two chamber manifold. The third, upper chamber is added to perform a calibration procedure for the peristaltic pump actuator. In a first step of the calibration procedure, fresh dialysis fluid is pulled from one of the dialysis fluid containers to prime the middle and lower chambers completely, as determined using the capacitance sensors, so that all air is pushed to drain. In a next step, the pinch valve for the branch line leading from the first dialysis fluid container to the lower chamber is opened, and the peristaltic pump actuator is actuated at a known revolutions per minute ("rpm") in a first direction so as to move dialysis fluid from the middle chamber to the lower chamber until the middle chamber is completely empty as determined by the associated capacitance sensor, wherein fluid in the lower chamber migrates back through the open branch line into the first dialysis fluid container, air from the upper chamber is pulled into the middle chamber, and the flexible sheet covering the third chamber bows inward into the upper chamber to compensate for the air that moves from the upper chamber to the middle chamber. The volume of the middle chamber ($V_m$) is known and the time duration ($\Delta t$) needed to fully drain the middle chamber is measured. Knowing those two parameters and the rpm of the pump actuator actuated in the draining direction allows the stroke volume per revolution in the chamber draining direction to be calculated, namely, to be equal to $V_m/\Delta t/rpm$, e.g., in milliliters ("ml")/rpm.

In a next step, wherein the pinch valve for the branch line leading from the first dialysis fluid container to the lower chamber remains open, and the peristaltic pump actuator is actuated at a known revolutions per minute ("rpm") in a second direction so as to move dialysis fluid from the lower chamber to the middle chamber until the middle chamber is completely full as determined by the associated capacitance sensor, wherein fluid from the first dialysis fluid container flows through the open branch line into the lower chamber and from the lower chamber to the middle chamber, air is pushed from the middle chamber into the upper chamber, and the flexible sheet covering the upper chamber straightens within the upper chamber due to the air being pushed into the upper chamber by the dialysis fluid entering the middle chamber. The volume of the middle chamber ($V_m$) is known and the time duration ($\Delta t$) needed to fully fill the middle chamber is measured. Knowing those two parameters and the rpm of the pump actuator actuated in the chamber filling direction allows the stroke volume per revolution in the filling direction to be calculated, namely, to be equal to $V_m/\Delta t/rpm$, e.g., in ml/rev.

Alternative rigid plastic manifolds are discussed herein for providing unlimited air into the corresponding manifold assemblies. A first alternative manifold adds a dedicated air port to the top chamber. Connected to the port is a tube and connector containing a hydrophobic air filter. A pinch valve is added to the cycler for selectively opening and closing the air filter line, which is normally closed. The pinch valve may be opened at any time air is needed for volumetric calibration, wherein the peristaltic pump is used to draw in air into, e.g., the upper chamber of the first alternative unlimited air manifolds.

A second alternative unlimited air manifold provides a dedicated air port on the back of the manifold. The air port is routed to the top chamber of the manifold via an air pathway. A hydrophobic air filter is attached to the air port. The cycler provides a seal, e.g., a spring closed and pneumatically opened seal, to normally seal the hydrophobic air filter closed. The cycler provides a pneumatic pump and possibly a pneumatic supply tank to supply, e.g., negative pressure to overcome the spring force and open the seal to expose the hydrophobic filter. The cycler accordingly includes at least one pneumatic valve to open and close a pneumatic line leading to the seal. The pneumatic valve is normally closed until air is needed in the manifold for a volumetric calibration. The peristaltic pump is used again to draw in air into the top chamber at any time and for any amount of air needed for the volumetric calibration.

The APD cycler of the present disclosure includes a control unit having one or more processor, one or more memory and a video controller that controls a user interface, such as a touch screen user interface. The control unit receives signals from the capacitance sensors and is programmed to use the signals to look for air during treatment and to run any one or more of the calibration procedures discussed here. The control unit receives signals from other sensors, such as pressure sensors and temperature sensors, and is programmed for example to use (i) pressure sensor signals as feedback to control the motor for the peristaltic pump actuator to pump at or below safe positive and negative patient pressure limits and (ii) temperature sensor signals to control the dialysis fluid heater to heat fresh dialysis fluid within the first dialysis fluid container to body temperature, e.g., 37° C.

The control unit is configured to use the results of the peristaltic pump calibration procedures discussed herein in determining how much fresh PD fluid is delivered to the patient and how much used PD fluid is removed from the patient. That is, knowing the latest volume per revolution, the control unit counts the number of revolutions over a patient fill or patient drain (including partial revolutions) and multiplies that number by the volume per revolution to determine the volume of fluid filled or drained. It should be appreciated that the volume per revolution could instead be weight per revolution (grams/rev) where the weight of fresh or used dialysis fluid within a particular chamber of the manifold is known.

It is contemplated to perform any of the calibration procedures discussed herein prior to treatment to calibrate the peristaltic pump in both counterclockwise and clockwise directions. The control unit may then initially attempt to drain the patient. If no effluent is present initially, the control unit senses same and moves directly to a first patient fill. After the first fill and during a first patient dwell, and during all subsequent patient dwells, the control unit repeats the calibration procedure to recalibrate the peristaltic pump in both counterclockwise and clockwise directions. Patient fills and drains may be performed using pressure and flow profiles, wherein lower pressures and flowrates are used initially, followed by higher pressures and flowrates, e.g., for 80% to 90% of the patient fill or drain, and possibly followed by a wind down period at the end of the patient fill or drain in which lower pressures and flowrates are used again.

The control unit also includes a transceiver and a wired or wireless connection to a network, e.g., the internet, for sending treatment data to and receiving prescription instructions from a doctor's or clinician's server interfacing with a doctor's or clinician's computer. In particular, the control unit may send data over the network regarding an analysis of the patient's effluent, wherein the data is used to determine the effectiveness of the patient's APD treatment. The doctor or clinician may review the data to determine if the patient's prescription should be modified, e.g., dwell times modified and/or change in dialysis fluid formulation. The data sent from the APD cycler to the network may be the same as, or akin to, data obtained from a peritoneal equilibration test ("PET").

PETs determine the mass transport characteristics associated with the patient's peritoneum. PETs help doctors and clinicians to decide whether a patient's PD treatment may be improved, e.g., using different dwell times and/or different PD fluid formulation. A full PET may take around five hours to complete and may involve a CAPD exchange for example using a 2.27% glucose solution. Samples of PD fluid and patient blood are taken at set times. It is known that classical parameters of peritoneal transport such as glucose reabsorption and creatinine transport have a direct correlation with the ionic conductivity of patient effluent. Conductivity has also been used to distinguish patients with and without ultrafiltration failure.

The capacitive sensing associated with the dual and three chamber rigid plastic manifolds of the present disclosure provides an opportunity determine the conductivity associated with both the fresh and used dialysis fluid and to use the measured and determined conductivities to develop data and send the data via a network to locations that have the need and ability to clinically analyze the data for the reasons discussed above. In particular, the capacitance sensors of the present manifolds provide a measure of a liquid dielectric constant from which a conductivity value can be derived.

One possible test procedure is to fill both chambers of the manifold with fresh dialysis fluid and then measure the capacitance ($f_{fresh}$). That fluid is drained after which both chambers of the manifold are filled with effluent and a second capacitance measurement is taken ($f_{effluent}$). The difference between the two readings ($\Delta f = f_{fresh} - f_{effluent}$) is determined, recorded in the memory of the APD cycler and sent via the network to the doctor's or clinician's computer for clinical analysis.

The peritoneal effectiveness evaluation is advantageous for at least three reasons. First, the evaluation may be performed on a regular basis, even per treatment or per patient drain if desired, without having to make the patient travel to have a test performed. Second, the test is easy to perform such that it does not unduly interrupt treatment. Third, the capacitance measurement is non-invasive, that is, it does not require a probe or electrode to contact the fluid being sensed as is the case with typical conductivity sensors. Sterility and cost issues with such contact are thus avoided.

In light of the disclosure set forth herein, and without limiting the disclosure in any way, in a first aspect, which may be combined with any other aspect described herein, or portion thereof, a peritoneal dialysis ("PD") system comprises a cycler including an actuation surface having a peristaltic pump actuator; a manifold assembly including a rigid manifold having first and second chambers, the rigid manifold configured and arranged to be abutted against the actuation surface for operation, a peristaltic pump tube extending from the first chamber to the second chamber of the rigid manifold, a dialysis fluid container line extending from the first chamber, and a branch line extending between the dialysis fluid container line and the second chamber; and a control unit configured to cause the peristaltic pump actuator to actuate the peristaltic pump tube to pump dialysis fluid from the branch line into the second chamber and from the second chamber into the first chamber.

In a second aspect, which may be combined with any other aspect described herein, or portion thereof, when the rigid manifold is abutted against the actuation surface for operation, the first chamber is an upper chamber and the second chamber is a lower chamber.

In a third aspect, which may be combined with any other aspect described herein, or portion thereof, the rigid manifold includes at least one flexible sheet surface.

In a fourth aspect, which may be combined with any other aspect described herein, or portion thereof, at least one of the first and second chambers of the rigid manifold includes at least one peg extending inwardly to prevent the flexible sheet from collapsing under negative pressure.

In a fifth aspect, which may be combined with any other aspect described herein, or portion thereof, at least one of the first or second chambers of the rigid manifold includes a pressure sensing hole and a pressure sensing membrane covering the pressure sensing hole, the at least one pressure sensing membrane placed in registry with a corresponding at least one pressure transducer when the rigid manifold is abutted against the actuation surface for operation.

In a sixth aspect, which may be combined with any other aspect described herein, or portion thereof, the PD system includes an air channel extending from one of the first or second chambers to a pressure sensing hole and a hydrophobic filter covering the pressure sensing hole, the hydrophobic filter placed in registry with a corresponding pressure transducer when the rigid manifold is abutted against the actuation surface for operation, and wherein the hydrophobic filter allows for direct pressure communication between the air channel and the pressure transducer.

In a seventh aspect, which may be combined with any other aspect described herein, or portion thereof, the PD system includes a drain line extending from the first chamber of the rigid manifold, and wherein the control unit is configured to cause the peristaltic pump actuator to actuate the peristaltic pump tube to pump dialysis fluid from the branch line into the second chamber, from the second chamber into the first chamber, and from the first chamber into the drain line.

In an eighth aspect, which may be combined with any other aspect described herein, or portion thereof, the dialysis fluid container line is a first dialysis fluid container line, and which includes a second dialysis fluid container line extending from the second chamber, and wherein the control unit is configured to cause the peristaltic pump actuator to actuate the peristaltic pump tube to pump dialysis fluid from the branch line into the second chamber and from the second chamber into the first chamber when (i) first dialysis fluid remains in a first dialysis fluid container in fluid communication with the first dialysis fluid container line after a patient fill and (ii) second dialysis fluid provided in a second dialysis fluid container in fluid communication with the second dialysis fluid container line for a next patient fill is different than the first dialysis fluid.

In a ninth aspect, which may be combined with any other aspect described herein, or portion thereof, the dialysis fluid container line is a first dialysis fluid container line, and which includes a second dialysis fluid container line extending from the second chamber, and wherein the control unit is further configured to cause the peristaltic pump actuator to actuate the peristaltic pump tube to pump dialysis fluid from a second dialysis fluid container in fluid communication with the second dialysis fluid container line into a first dialysis fluid container in fluid communication with the first dialysis fluid container line for heating the second dialysis fluid.

In a tenth aspect, which may be combined with any other aspect described herein, or portion thereof, the cycler further includes a dialysis fluid heater, the manifold assembly configured such that a dialysis fluid container in fluid communication with the dialysis fluid container line is placed on the dialysis fluid heater for treatment.

In an eleventh aspect, which may be combined with any other aspect described herein, or portion thereof, the PD system includes a patient line extending from the second chamber of the rigid manifold, and wherein the cycler includes an air sensor positioned and arranged at the actuation surface to operate with the patient line when the rigid manifold is abutted against the actuation surface for operation.

In a twelfth aspect, which may be combined with any other aspect described herein, or portion thereof, the cycler includes a dialysis fluid container line valve and a branch line valve positioned and arranged at the actuation surface to operate with the dialysis fluid container line and the branch line, respectively, when the rigid manifold is abutted against the actuation surface for operation.

In a thirteenth aspect, which may be combined with any other aspect described herein, or portion thereof, the PD system includes at least one pair of capacitive sensing plates operable with at least one of the first chamber or the second chamber of the rigid manifold when abutted against the actuation surface for operation, and wherein the control unit is configured to receive a signal from each of the at least one pair of capacitive sensing plates, the at least one signal indicative of an amount of air in at least one of the first or second chambers.

In a fourteenth aspect, which may be combined with any other aspect described herein, or portion thereof, the cycler includes a door that encloses the rigid manifold after the rigid manifold is abutted against the actuation surface for operation, the actuation surface containing one of the plates of the at least one pair of capacitive sensing plates, and the door containing the other plate of the at least one pair of capacitive sensing plates.

In a fifteenth aspect, which may be combined with any other aspect described herein, or portion thereof, the at least one capacitive sensing plate contained by the actuation surface is parallel to and directly opposes the at least one capacitive sensing plate contained by the door.

In a sixteenth aspect, which may be combined with any other aspect described herein, or portion thereof, the rigid manifold includes a third chamber, the third chamber configured to at least one of (i) provide air for backfilling the first chamber when fluid is pumped from the first chamber to the second chamber during a calibration procedure for the peristaltic pump actuator or (ii) accept air from the first chamber when fluid is pumped from the second chamber to the first chamber during the calibration procedure for the peristaltic pump actuator.

In a seventeenth aspect, which may be combined with any other aspect described herein, or portion thereof, a peritoneal dialysis ("PD") system comprises a cycler including an actuation surface having a peristaltic pump actuator, and at least one pair of capacitive sensing plates; a manifold assembly including a rigid manifold having first and second chambers, the rigid manifold configured and arranged to be abutted against the actuation surface for operation, wherein the at least one pair of capacitive sensing plates is positioned to be operable with at least one of the first chamber or the second chamber, and a peristaltic pump tube extending from the first chamber to the second chamber of the rigid manifold; and a control unit configured to (i) cause the peristaltic pump actuator to actuate the peristaltic pump tube to pump an amount of dialysis fluid from the second chamber to the first chamber, (ii) receive a signal from each of the at least one pair of capacitive sensing plates, the at least one signal indicative of the amount of dialysis fluid pumped, (iii) count a number of revolutions of the peristaltic pump actuator needed to pump the amount of dialysis fluid from the second chamber to the first chamber, (iv) determine a current volume per revolution for the peristaltic pump actuator, and (v) use the current volume per revolution for at least one subsequent operation of the peristaltic pump actuator.

In an eighteenth aspect, which may be combined with any other aspect described herein, or portion thereof, the current volume per revolution is for a first direction of the peristaltic pump actuator, and wherein the control unit is further configured to (vi) cause the peristaltic pump actuator to actuate the peristaltic pump tube in a second direction to pump another amount of dialysis fluid from the first chamber to the second chamber, (vii) receive a signal from each of the at least one pair of capacitive sensing plates, the at least one signal indicative of the other amount of dialysis fluid pumped, (viii) count a number of revolutions of the peristaltic pump actuator needed to pump the other amount of dialysis fluid from the first chamber to the second chamber, (ix) determine a current volume per revolution for a second direction of the peristaltic pump actuator, and (x) use the current volume per revolution for at least one subsequent operation of the peristaltic pump actuator in the second direction.

In a nineteenth aspect, which may be combined with any other aspect described herein, or portion thereof, the first direction is a patient drain direction and the second direction is a patient fill direction.

In a twentieth aspect, which may be combined with any other aspect described herein, or portion thereof, the first direction is also a to-dialysis fluid heater direction.

In a twenty-first aspect, which may be combined with any other aspect described herein, or portion thereof, the rigid manifold includes a third chamber, the third chamber configured to provide air for backfilling the first chamber when the other amount of dialysis fluid is pumped from the first chamber to the second chamber.

In a twenty-second aspect, which may be combined with any other aspect described herein, or portion thereof, the rigid manifold includes a third chamber, the third chamber configured to accept air from the first chamber when the amount of dialysis fluid is pumped from the second chamber to the first chamber.

In a twenty-third aspect, which may be combined with any other aspect described herein, or portion thereof, the control unit is configured to repeat (i) to (v) of the seventeenth aspect in each of a plurality of cycles of a PD treatment.

In a twenty-fourth aspect, which may be combined with any other aspect described herein, or portion thereof, the number of revolutions takes into account a fraction of a revolution.

In a twenty-fifth aspect, which may be combined with any other aspect described herein, or portion thereof, the control unit is configured to perform (i) to (v) of the seventeenth aspect when a threshold amount of air is sensed in one of the first or second chambers of the rigid manifold.

In a twenty-sixth aspect, which may be combined with any other aspect described herein, or portion thereof, the PD system includes a first pair of capacitive sensing plates operable with the first chamber and a second pair of sensing plates operable with the second chamber, and wherein the control unit is configured in (ii) of the seventeenth aspect to receive a first signal from the first pair of capacitive sensing plates, the first signal indicative of the amount of dialysis fluid pumped to the first chamber, and to receive a second signal from the second pair of capacitive sensing plates, the second signal indicative of the amount of dialysis fluid pumped from the second chamber.

In a twenty-seventh aspect, which may be combined with any other aspect described herein, or portion thereof, the control unit is configured to at least one of (i) determine a degree to which the first and second signals match, or (ii) average the first and second signals.

In a twenty-eighth aspect, which may be combined with any other aspect described herein, or portion thereof, the cycler includes a door that encloses the rigid manifold after the rigid manifold is abutted against the actuation surface for operation, the actuation surface containing one of the plates of the at least one pair of capacitive sensing plates, and the door containing the other plate of the at least one pair of capacitive sensing plates.

In a twenty-ninth aspect, which may be combined with any other aspect described herein, or portion thereof, the at least one capacitive sensing plate contained by the actuation surface is parallel to and directly opposes the at least one capacitive sensing plate contained by the door.

In a thirtieth aspect, which may be combined with any other aspect described herein, or portion thereof, using the current volume per revolution for at least one subsequent operation of the peristaltic pump actuator includes multiplying the volume per revolution by a number of revolutions recorded by the control unit during each of the at least one subsequent operation.

In a thirty-first aspect, which may be combined with any other aspect described herein, or portion thereof, the control unit includes at least one processor, at least one memory and may include at least one video controller.

In a thirty-second aspect, which may be combined with any other aspect described herein, or portion thereof, a peritoneal dialysis ("PD") system comprises a cycler including an actuation surface having a peristaltic pump actuator, and at least one pair of capacitive sensing plates; a manifold assembly including a rigid manifold having at least one chamber, the rigid manifold configured and arranged to be abutted against the actuation surface for operation, wherein the at least one pair of capacitive sensing plates is positioned to be operable with the at least one chamber of the rigid manifold, and a peristaltic pump tube including first and second ends in fluid communication with the rigid manifold; and a control unit configured to (i) cause the peristaltic pump actuator to actuate the peristaltic pump tube to pump an amount of dialysis fluid to one of the at least one chamber, (ii) receive a signal from the pair of capacitive sensing plates associated with the chamber, the signal indicative of the amount of dialysis fluid pumped, (iii) count a number of revolutions of the peristaltic pump actuator needed to pump the amount of dialysis fluid to the chamber, (iv) determine a current volume per revolution for the peristaltic pump actuator, and (v) use the current volume per revolution for at least one subsequent operation of the peristaltic pump actuator.

In a thirty-third aspect, which may be combined with any other aspect described herein, or portion thereof, the current volume per revolution is for a first direction of the peristaltic pump actuator, and wherein the control unit is further configured to (vi) cause the peristaltic pump actuator to actuate the peristaltic pump tube in a second direction to pump another amount of dialysis fluid from the chamber, (vii) receive a signal from the pair of capacitive sensing plates associated with the chamber, the signal indicative of the other amount of dialysis fluid pumped, (viii) count a number of revolutions of the peristaltic pump actuator needed to pump the other amount of dialysis fluid from the chamber, (ix) determine a current volume per revolution for a second direction of the peristaltic pump actuator, and (x) use the current volume per revolution for at least one subsequent operation of the peristaltic pump actuator in the second direction.

In a thirty-fourth aspect, which may be combined with any other aspect described herein, or portion thereof, the control unit is configured to repeat (i) to (v) of the thirty-second aspect in each of a plurality of cycles of a PD treatment.

In a thirty-fifth aspect, which may be combined with any other aspect described herein, or portion thereof, the PD system is configured to exchange at least one of treatment or patient data over a network.

In a thirty-sixth aspect, which may be combined with any other aspect described herein, or portion thereof, the control unit is configured to perform (i) to (v) of the thirty-second aspect when a threshold amount of air is sensed in the chamber of the rigid manifold.

In a thirty-seventh aspect, which may be combined with any other aspect described herein, or portion thereof, the cycler includes a door that hinges closed against the rigid manifold after the rigid manifold is abutted against the actuation surface for operation, the actuation surface containing one of the plates of the at least one pair of capacitive sensing plates, and the door containing the other plate of the at least one pair of capacitive sensing plates.

In a thirty-eighth aspect, which may be combined with any other aspect described herein, or portion thereof, the at least one capacitive sensing plate contained by the actuation surface is at least one of parallel to and directly opposing the at least one capacitive sensing plate contained by the door.

In a thirty-ninth aspect, which may be combined with any other aspect described herein, or portion thereof, using the current volume per revolution for at least one subsequent operation of the peristaltic pump actuator includes mathematically combining the volume per revolution by a number of revolutions recorded by the control unit during each of the at least one subsequent operation.

In a fortieth aspect, which may be combined with any other aspect described herein, or portion thereof, the cycler includes a dialysis fluid heater.

In a forty-first aspect, which may be combined with any other aspect described herein, or portion thereof, a peritoneal dialysis ("PD") system comprises a cycler including an actuation surface having a peristaltic pump actuator, and a pair of capacitive sensing plates; a manifold assembly including a rigid manifold having first, second and third chambers, the rigid manifold configured and arranged to be abutted against the actuation surface for operation, wherein the pair of capacitive sensing plates is positioned to be operable with the first chamber, and a peristaltic pump tube extending from the first chamber to the second chamber of the rigid manifold; and a control unit configured to (i) cause the peristaltic pump actuator to actuate the peristaltic pump tube at a known revolutions per minute ("rpm") to empty dialysis fluid from a full first chamber to the second chamber, wherein air backfills the first chamber from the third chamber, (ii) receive a signal from the pair of capacitive sensing plates indicating that the first chamber is empty, (iii) record a time duration $\Delta t$ needed to empty dialysis fluid from the full first chamber to the second chamber, (iv) determine a current volume per revolution for the peristaltic pump actuator by performing a first division of a known volume of the first chamber by the time duration $\Delta t$ and a second division of a result of the first division by the known rpm, and (v) use the current volume per revolution for at least one subsequent operation of the peristaltic pump actuator.

In a forty-second aspect, which may be combined with any other aspect described herein, or portion thereof, the control unit is configured use the signal from the pair of capacitive sensing plates to confirm that the first chamber is full of dialysis fluid prior to (i) of the forty-first aspect.

In a forty-third aspect, which may be combined with any other aspect described herein, or portion thereof, the current volume per revolution is for a first direction of the peristaltic pump actuator, and wherein the control unit is further configured to (vi) cause the peristaltic pump actuator to actuate the peristaltic pump tube at a known revolutions per minute ("rpm") in a second direction to fill first chamber with dialysis fluid from the second chamber, wherein the third chamber accepts air displaced from the first chamber, (ii) receive a signal from the pair of capacitive sensing plates indicating that the first chamber is full, (iii) record a time duration $\Delta t$ needed to fill dialysis fluid from the second chamber to the first chamber, (iv) determine a current volume per revolution for the peristaltic pump actuator in the second direction by performing a first division of a known volume of the first chamber by the time duration $\Delta t$ and a second division of a result of the first division by the known rpm, and (v) use the current volume per revolution in the second direction for at least one subsequent operation of the peristaltic pump actuator.

In a forty-fourth aspect, which may be combined with any other aspect described herein, or portion thereof, the first direction is a patient fill direction and the second direction is a patient drain direction.

In a forty-fifth aspect, which may be combined with any other aspect described herein, or portion thereof, the control unit is configured to repeat (i) to (v) of the forty-first aspect in each of a plurality of cycles of a PD treatment.

In a forty-sixth aspect, which may be combined with any other aspect described herein, or portion thereof, the cycler includes at least one valve opening or closing at least one tube or line extending from the rigid manifold.

In a forty-seventh aspect, which may be combined with any other aspect described herein, or portion thereof, the at least one valve is a pinch valve.

In a forty-eighth aspect, which may be combined with any other aspect described herein, or portion thereof, a dialysis fluid container in fluid communication with the rigid manifold operates as a dialysis fluid heating container.

In a forty-ninth aspect, which may be combined with any other aspect described herein, or portion thereof, an encoder is provided for use with the peristaltic pump actuator, wherein the encoder allows a full revolution of 360° of the actuator to be divided into many fractions of a rotation, e.g., into 5919 fractions.

In a fiftieth aspect, which may be combined with any other aspect described herein, or portion thereof, a peritoneal dialysis ("PD") system comprises a cycler including an actuation surface having a peristaltic pump actuator, and at least one pair of capacitive sensing plates; a manifold assembly including a rigid manifold having at least one chamber, the rigid manifold configured and arranged to be abutted against the actuation surface for operation, wherein the at least one pair of capacitive sensing plates is positioned to be operable with the at least one chamber of the rigid manifold, and a peristaltic pump tube including first and second ends in fluid communication with the rigid manifold; and a control unit configured to (i) cause the peristaltic pump actuator to actuate the peristaltic pump tube to fill one of the at least one chamber with fresh dialysis fluid, (ii) take a first reading from the pair of capacitive sensing plates associated with the chamber, the first reading indicative of a capacitance ($f_{fresh}$) associated with the chamber filled with fresh dialysis fluid, (iii) cause the peristaltic pump actuator to actuate the peristaltic pump tube to fill the chamber with effluent, (iv) take a second reading from the pair of capacitive sensing plates associated with the chamber, the second reading indicative of a capacitance ($f_{effluent}$) associated with the chamber filled with effluent, and (v) determine a difference ($\Delta f$) between the first and second readings.

In a fifty-first aspect, which may be combined with any other aspect described herein, or portion thereof, (iii) and (iv) occur before (i) and (ii) of the fiftieth aspect.

In a fifty-second aspect, which may be combined with any other aspect described herein, or portion thereof, the control unit is further configured to convert the difference between the first and second readings ($\Delta f$) into peritoneal dialysis effectiveness data or send the difference between the first and second readings ($\Delta f$) to a remote location for conversion into dialysis effectiveness data.

In a fifty-third aspect, which may be combined with any other aspect described herein, or portion thereof, a peritoneal dialysis ("PD") system comprises a cycler including an actuation surface having a peristaltic pump actuator, and at least one pair of capacitive sensing plates; a manifold assembly including a rigid manifold including a chamber, the rigid manifold configured and arranged to be abutted against the actuation surface for operation, wherein the at least one pair of capacitive sensing plates is positioned to be operable with the chamber of the rigid manifold, and an air port for allowing air into the chamber, and a peristaltic pump tube including first and second ends in fluid communication with the rigid manifold; and a control unit configured to (i) cause the peristaltic pump actuator to pull air into the chamber via the air port, (ii) cause the peristaltic pump actuator to actuate the peristaltic pump tube to pump an amount of dialysis fluid to the chamber to displace the air, (ii) receive a signal from the pair of capacitive sensing plates associated with the chamber, the signal indicative of the amount of dialysis fluid pumped, (iii) count a number of revolutions of the peristaltic pump actuator needed to pump the amount of dialysis fluid to the chamber, (iv) determine a current volume per revolution for the peristaltic pump actuator based on the counted number of revolutions, and (v) use the current volume per revolution for at least one subsequent operation of the peristaltic pump actuator.

In a fifty-fourth aspect, which may be combined with any other aspect described herein, or portion thereof, the manifold assembly includes an air port line in fluid communication with the air port, and which includes a hydrophobic filter located at a distal end of the air port line.

In a fifty-fifth aspect, which may be combined with any other aspect described herein, or portion thereof, the cycler includes an air port valve operating with the air port line, and wherein the control unit is configured to open the air port valve during (i) of the fifty-third aspect.

In a fifty-sixth aspect, which may be combined with any other aspect described herein, or portion thereof, the PD system includes a hydrophobic filter attached to the air port, wherein the cycler includes a seal operating with the hydrophobic filter, and wherein the control unit is configured to remove the seal from the hydrophobic filter during (i) of the fifty-third aspect.

In a fifty-seventh aspect, which may be combined with any other aspect described herein, or portion thereof, the control unit is configured to open a pneumatic valve to allow negative pressure to remove the seal from the hydrophobic filter.

In a fifty-eighth aspect, which may be combined with any other aspect described herein, or portion thereof, the PD system includes an air line extending from the chamber to a hydrophobic filter allowing direct pressure communication between fresh or used dialysis fluid in the chamber and a pressure transducer provided by the cycler.

In a fifty-ninth aspect, which may be combined with any other aspect described herein, or portion thereof, any of the features, functionality and alternatives described in connection with any one or more of FIGS. 1 to 19 may be combined with any of the features, functionality and alternatives described in connection with any other of FIGS. 1 to 19.

It is accordingly an advantage of the present disclosure to provide an APD system having a manifold assembly and peristaltic pump.

It is another advantage of the present disclosure to provide an APD system that is portable to ultra-portable.

It is a further advantage of the present disclosure to provide an APD system that eliminates certain sealing issues present in known APD systems.

It is yet a further advantage of the present disclosure to provide an APD pump driven system that eliminates bulky pneumatic equipment associated with certain APD systems.

It is yet another advantage of the present disclosure to provide an APD system that manages peritoneal dialysis fluid flow so as to be within safe and comfortable patient pressure limits.

It is still a further advantage of the present disclosure to provide an APD system that provides non-invasive peristaltic pump actuator calibration.

It is still another advantage of the present disclosure to provide an APD system that provides an improved way of obtaining peritoneal effectiveness data.

Additional features and advantages are described in, and will be apparent from, the following Detailed Description and the Figures. The features and advantages described herein are not all-inclusive and, in particular, many additional features and advantages will be apparent to one of ordinary skill in the art in view of the figures and description. Also, any particular embodiment does not have to have all of the advantages listed herein and it is expressly contemplated to claim individual advantageous embodiments separately. Moreover, it should be noted that the language used in the specification has been selected principally for readability and instructional purposes, and not to limit the scope of the inventive subject matter.

BRIEF DESCRIPTION OF THE FIGURES

FIGS. 2A to 2C are front, back and perspective views of one embodiment for a disposable rigid plastic manifold of the APD system of the present disclosure.

FIGS. 14A and 14B illustrate a second embodiment for providing an unlimited source of air to the disposable rigid plastic manifold of the present disclosure.

DETAILED DESCRIPTION

Figure 1:
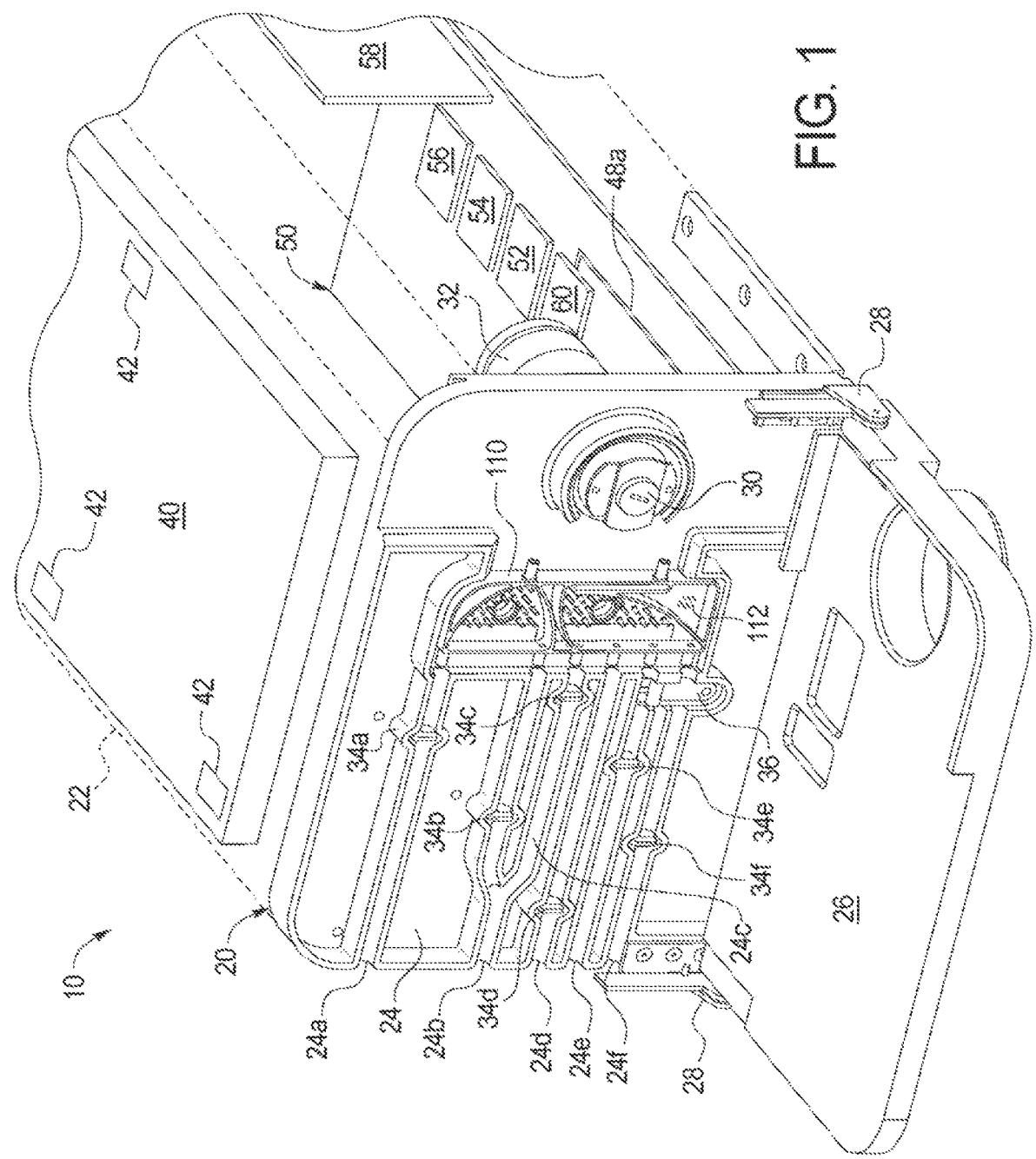
FIG. 1 is a perspective view of one embodiment for an actuation surface and rotatable door of an automated peritoneal dialysis ("APD") cycler operating with a disposable rigid plastic manifold of the APD system of the present disclosure.

Referring now to the drawings and in particular to FIGS. 1 and 2A to 2C, an embodiment of system 10 includes an automated peritoneal dialysis ("APD") cycler 20 having a housing 22, which uses peristaltic pumping in the illustrated embodiment and operates with a manifold assembly 100 (FIG. 3) that organizes tubing and performs many functions discussed herein. Manifold assembly 100 includes a rigid plastic manifold 110, which in an embodiment is covered on one side by a flexible plastic sheet 112 for its for ease and cost of manufacturing. In an alternative embodiment, plastic sheet 112 is instead a rigid lid, which is, for example, ultrasonically welded to the rest of rigid manifold 110. Here, rigid lid 112 may include a slight ridge around its perimeter, which aids in the rigidity of the lid. Rigid plastic manifold 110, plastic sheet 112 (flexible or rigid), the fluid lines and fluid containers (discussed below) of manifold assembly 100 may be made of one or more plastic, e.g., polyvinylchloride ("PVC") or a non-PVC material, such as polyethylene ("PE"), polyurethane ("PU") or polycarbonate ("PC"). Housing 22 of cycler 20 may be made of any of the above plastics, and/or of metal, e.g., stainless steel, steel and/or aluminum.

As illustrated in FIG. 1, rigid plastic manifold 110 is mounted inside of APD cycler 20, for example, in between an actuation surface 24 and a door 26 of the APD cycler. Door, for example, hinges open via one or more hinge 28 located along a bottom of cycler housing 22, adjacent to actuation surface 24. In the illustrated implementation, rigid plastic manifold 110 of manifold assembly 100 is mounted so that plastic sheet 112 of manifold 110 is located on the surface facing door 26 (when closed), and so that manifold 110 is constrained by the door during operation.

APD cycler 20 includes a peristaltic pump head or actuator 30, which is able to be actuated in two directions by a motor 32, e.g., a stepper or brushed or brushless DC motor, located within housing of the APD cycler. In an embodiment, electrical current supplied to motor 32 may be varied for pressure control. For example, the current may be limited so that pumping pressure to the patient for a patient fill is at or below a positive pressure threshold, e.g., 3 to 5 psig. The current may be limited so that pumping pressure from the patient for a patient drain is at or below a negative pressure threshold, e.g., −1.5 to −3 psig. The current may be higher for other pumping operations, e.g., positive pressure to drain and positive pressure to a dialysis fluid heating container, e.g., 7 psig.

Pinch valves 34a to 34f are provided along the actuation surface of APD cycler 20 to selectively occlude tubing that extends from the rigid plastic manifold. Tubing is discussed in detail below, but generally, pinch valve 34a is a drain line pinch valve. Pinch valve 34b is a first dialysis fluid container/heating container valve. Pinch valve 34c is a Y-connection or branch line valve. Pinch valve 34d is a second dialysis fluid container valve. Pinch valve 34e is a third dialysis fluid container valve. Pinch valve 34f is a patient line valve. Pinch valves 34a to 34f are in one fail safe embodiment energized open and de-energized closed, electrically actuated pinch valves. In one embodiment, the inner surface of door 26 provides the surface against which pinch valves 34a to 34f occlude their respective tubing.

In the illustrated embodiment, actuation surface 24 defines grooves 24a to 24f for fitting and organizing the tubes of manifold assembly 100. Pinch valves 34a to 34f are located along grooves 24a to 24f, respectively. Groove 24f of actuation surface 24 is also illustrated operating with an optional air sensor 36, behind where the patient line is mounted for operation. As discussed in detail below, air is detected within rigid plastic manifold 110 and thus air sensor 36 is not be needed. Air sensor 36 may however be provided in addition to the capacitance air sensing discussed herein, e.g., as a last check before fresh, heated dialysis fluid is delivered to the patient. Air sensor 36 may also be provided if the capacitance air sensing discussed herein is not employed.

When rigid plastic manifold 110 is mounted to actuation surface 24 for operation, ports for receiving tubes extend from both sides of the manifold, e.g., from the right and left sides of the manifold. Ports from one side of manifold 110 (e.g., the left side viewing APD cycler from the front in FIG. 1) are, for example, from top to bottom, a drain port 114a, a first heater line/first dialysis fluid container port 114b, a bypass or branch line port 114c, a second dialysis fluid container port 114d, a third dialysis fluid container port 114e and a patient line port 114f. Ports 114g and 114h extending from the other side of manifold 110 (e.g., right side viewing APD cycler from the front in FIG. 1) connect sealingly to a peristaltic pumping tube 124*gh* (see FIG. 3), which is actuated by peristaltic pump actuator 30.

Rigid plastic manifold 110 includes a rigid plastic wall 116 that opposes plastic sheet 112. Rigid plastic wall 116 abuts up against actuation surface 24 for operation. One or more apertures 118*a* and 118*b*, such as circular holes, are formed or provided in rigid plastic wall 116. Circular holes 118*a* and 118*b* are covered with pressure sensing membranes. When manifold 110 is mounted to APD cycler 20 for operation, the pressure sensing membranes covering holes 118*a* and 118*b* abut against pressure transducers (not illustrated) provided by the cycler at actuation surface 24. The pressure sensors or transducers sense the pressure of fresh and used dialysis fluid entering and leaving the manifold, which is used as feedback for the electrical current control of motor 32 to regulate fluid pumping pressures as discussed above.

A pressure sensing hole and accompanying pressure sensing membrane 118*a* and 118*b* is provided respectively in each of an upper chamber 110*a* and a lower chamber 110*b* of rigid plastic manifold 110. First or upper chamber 110*a* is the primary air collecting chamber, which communicates with drain port 114*a* for removing air to drain (e.g., house drain or drain container). Lower chamber 110*b* communicates fluidly with lower-most patient line port 114*f*, which is the most important location to be free of air, wherein air in the lower chamber 10*b* naturally tends to buoy upwards away from patient line port 114*f*. The number of ports 114*a* to 114*f* provided by each of upper and lower chambers 110*a* and 10*b* are not limited by the number shown and described herein embodiment and may be more or less than shown and described for either or both chambers.

First or upper chamber 110*a* includes a wall or walls 120*a* that is/are curved to help aid dialysis fluid flow from drain or dialysis fluid/heater ports 114*a* and 114*b* to peristaltic pump port 114*g* or from peristaltic pump port 114*g* to dialysis fluid/heater ports 114*a* and 114*b*. Second or lower chamber 110*b* includes a wall 120*b* that extends up towards a top of lower chamber 110*b*, leaving a small gap G to allow dialysis fluid flow from branch line port 114*c*, dialysis fluid ports 114*d* or 114*e* or patient line port 114*f* to peristaltic pump port 114*h*, or from peristaltic pump port 114*h* to branch line port 114*c*, dialysis fluid ports 114*d* or 114*e* or patient line port 114*f*. Wall 120*b* forces the dialysis fluid to travel a longer, more tortuous path, allowing air more time and opportunity to migrate towards the top of second or lower chamber 110*b*. When a threshold amount of air is sensed in lower chamber 110*b*, peristaltic pump actuator 30 is caused to rotate counterclockwise in FIG. 1 to pump dialysis fluid to in turn push air from first or lower chamber 110*b* into second or upper chamber 110*a*, where it is removed to drain via drain port 114*a* and associated drain line.

Rigid plastic manifold 110 is molded, e.g., injection or blow molded to form first and second chambers 110*a* and 110*b*, apertures 118*a* and 118*b*, internal walls 120*a* and 120*b*, and pegs 122. In the illustrated embodiment, each of upper chamber 110*a* and lower chamber 110*b* of manifold 110 is provided with a plurality of pegs 122 extending inwardly from the rigid plastic wall 116, which prevent flexible plastic sheet 112 from collapsing under negative pressure. In the instance in which plastic sheet 112 is instead a rigid plastic lid, pegs 122 are not needed or provided.

Figure 3:
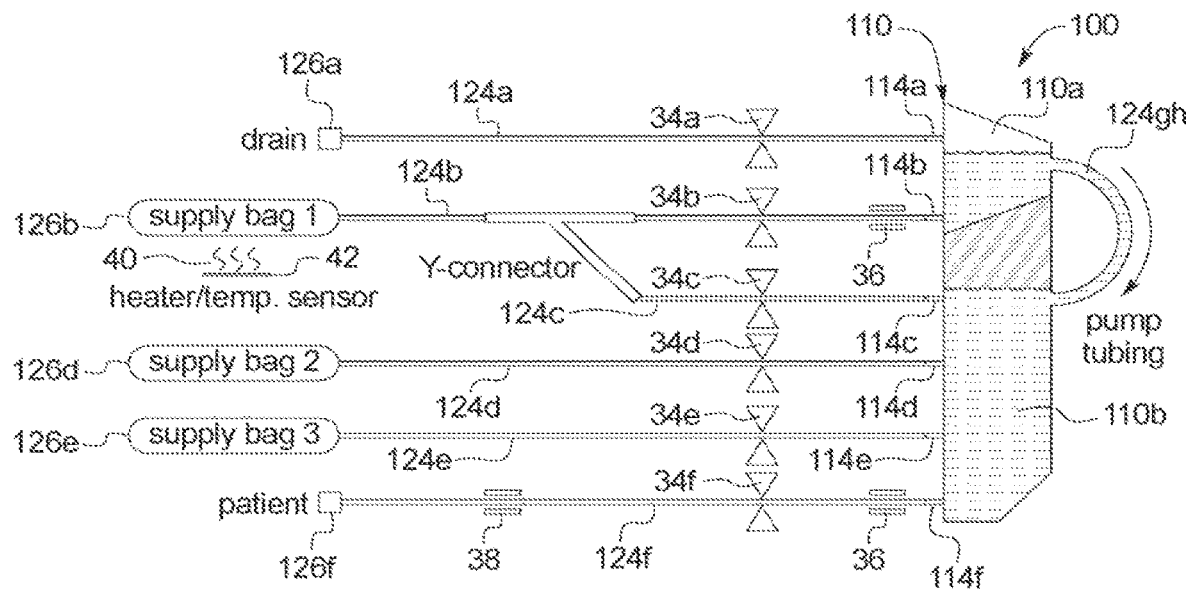
FIG. 3 is a front view illustrating one embodiment of a flow regime for the APD system of the plan view.

Referring additionally to FIG. 3, manifold assembly 100 is illustrated in more detail. A drain line 124*a* and first dialysis fluid container/heater line 124*b* extend and connect to their respective ports 114*a* and 114*b*, which communicate fluidly with upper chamber 110*a*. Drain line 124*a* and first dialysis fluid container/heater line 124*b* are routed respectively in grooves 24*a* and 24*b* of actuation surface 24 and are opened or occluded by respective valves 34*a* and 34*b*. A Y-connection or branch line 124*c*, a second dialysis fluid container line 124*d*, a third dialysis fluid container line 124*e* and a patient line 124*f* extend and connect to their respective ports 114*c* to 114*f*, which communicate fluidly with lower chamber 110*b*. Y-connection or branch line 124*c*, second dialysis fluid container line 124*d*, third dialysis fluid container line 124*e* and patient line 124*f* are routed respectively in grooves 24*c* to 24*f* of actuation surface 24 and are opened or occluded by respective valves 34*c* to 34*f*.

Peristaltic pumping tube 124*gh* or line extends between and connects to respective ports 114*g* and 114*h* of the upper chamber 110*a* and lower chamber 110*b*. In an embodiment, peristaltic pump actuator 30 located at the actuation surface of APD cycler 20 rotates in a first direction (clockwise in FIGS. 1 and 3) to pump fresh, heated dialysis fluid from upper chamber 110*a*, through the peristaltic pumping tube 124*gh*, to lower chamber 110*b*, and to the patient. Peristaltic pump actuator 30 rotates in the opposite direction (counterclockwise in FIGS. 1 and 3) to pump used dialysis fluid from lower chamber 110*b*, through the peristaltic pumping tube 124*gh*, to upper chamber 10*a*, and to drain (used dialysis fluid or effluent) or to a heater for heating (fresh dialysis fluid).

FIG. 3 also illustrates that manifold assembly 100 includes drain container 126*a* located at the distal end of drain tube or line 124*a*. Drain line 124*a* extends alternatively to a house drain, such as the patient's toilet, bathtub or sink. Fresh dialysis fluid containers 126*b*, 126*d* and 126*e* are located respectively at the distal ends of first, second and third dialysis fluid container lines 124*b*, 124*d* and 124*e*. Fresh dialysis fluid containers or bags 126*b*, 126*d* and 126*e* may hold different types and quantities of fresh dialysis fluid, such as different dextrose or glucose levels or formulations, e.g., container 126*e* may contain icodextrin, which is used for the patient's last fill. Containers 126*b* or 126*d* may for example hold multiple fill volume's worth of fresh dialysis fluid.

Patient line or tube 124*f* extends to a patient line connector 126*f*, which may for example connect to a patient's transfer set leading to an indwelling catheter that extends to the patient's peritoneal cavity. FIG. 3 also illustrates that in addition to air sensor 36, patient line or tube 124*f* may also operate with a pressure sensor 38, which may be provided alternatively or in addition to membranes covering holes 118*a* and 118*b* and operating with pressure transducers located at actuation surface 24 for controlling patient pumping pressure as has been discussed herein. A second air sensor 36 may also operate with dialysis fluid container/heater line 124*b* to look for air that comes out of solution due to the heating of the fresh dialysis fluid. First and second air sensors 36 may be provided alternatively to or in addition to the air detection via capacitance sensing discussed herein.

FIG. 3 schematically illustrates fresh dialysis fluid container or bag 126*b* operating with a dialysis fluid heater 40. FIG. 1 illustrates that heater 40 is located on top of housing 22 of cycler 20 in one embodiment. In an alternative embodiment, heater 40 may be located separate from housing 22, e.g., as a warming blanket or pouch. In either case, heater 40 is in one embodiment a resistive plate heater, which is configured to heat a fill volume's quantity of fresh dialysis fluid (e.g., one to two liters) from ambient temperature to body temperature (e.g., 37° C.), for example, during a current patient dwell phase so that heated dialysis fluid is ready as soon as the patient is drained after the current dwell phase. One or more temperature sensor 42 operates with heater 40 to provide feedback for controlling the heater, e.g., using a proportional, integral, derivative control algorithm.

In FIG. 3, peristaltic pump actuator 30 rotates in the counterclockwise direction to pump fresh dialysis fluid from either of the second or third dialysis fluid containers 126*d* or 126*e* into lower chamber 110*b*, through peristaltic pumping tube 124*gh*, to upper chamber 110*a*, and to the previously emptied first dialysis fluid container 126*d*, which is placed in operable communication with dialysis fluid heater 40. By allowing the fresh dialysis fluid from each of the dialysis fluid containers 126*b*, 126*d* and 126*e* to be heated in first dialysis fluid container or bag 126*b*, the disposable dialysis fluid set of manifold assembly 100 only has to be loaded once for operation. Additionally, a separate dialysis fluid heating container or bag is not needed.

In one embodiment, first dialysis fluid container or bag 126*b* is loaded onto dialysis fluid heater 40 for an initial patient fill. After first dialysis fluid container 126*b* is emptied, peristaltic pump actuator 30 reverses and pulls fresh dialysis fluid from second dialysis fluid container 126*d* and pushes same into first dialysis fluid container 126*b* for heating. The same procedure is performed for third dialysis fluid supply container 126*e* when second dialysis fluid supply container 126*d* is emptied. If the dialysis fluid from the second 126*d* (or third 126*e*) container is different than that of first container 126*b*, Y-connection or branch line 124*c* is used to enable the remaining fluid from first dialysis fluid container 126*b* to be pulled by the peristaltic pump actuator 30 into lower chamber 110*b* and then pushed into upper chamber 110*a* and out to drain 126*a* before the differently formulated fluid of the second 126*d* (or third 126*e*) dialysis fluid container is delivered to first dialysis fluid container 126*b* for heating. In the illustrated embodiment of FIG. 3, Y-connection or branch line 124*c* branches off dialysis fluid container/heater line 124*b*, e.g., via a Y-connector, and extends to bypass or branch line port 114*c* communicating with lower chamber 110*b*.

FIG. 2A illustrates that sensor portions 116*s* of the rigid plastic wall 116 for each of upper chamber 110*a* and lower chamber 110*b* are not provided with pegs 122 and serve as a capacitive sensing areas for the respective upper chamber 110*a* and lower chamber 110*b*. Each of the capacitive sensing portions 116*s* of the rigid plastic wall 116 during operation presses up against a capacitive sensing plate or electrode located along actuation 24 surface of APD cycler 20. Door 26 of APD cycler 20 is provided with a matching capacitive sensing plate or electrode for each chamber 110*a* and 110*b*, which each directly oppose the capacitive sensing plates located along actuation surface 24. The matching upper and lower sets or pairs of capacitive sensing plates or electrodes form upper and lower capacitive sensors. The capacitive sensors, one for each chamber 110*a* and 110*b*, detect an amount of air in the respective chamber. If too much air accumulates in chamber 110*a*, APD cycler 20 stops its current routine and causes peristaltic pump actuator 30 with drain line valve 34*a* open to rotate in a counterclockwise direction in FIG. 3 to push the air to drain 126*a* via drain line or tube 124*a*.

Figure 4:
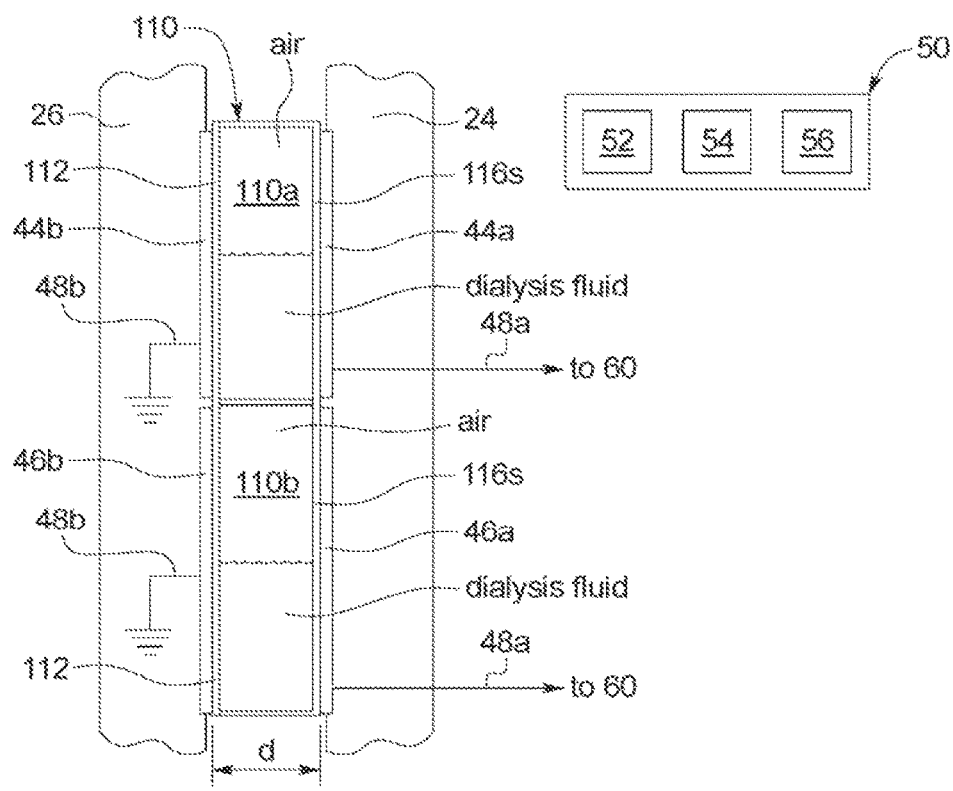
FIG. 4 is a side view of the disposable rigid plastic manifold illustrating schematically one embodiment for the capacitive sensing plates or electrodes of the present disclosure.

FIG. 4 illustrates rigid plastic manifold 110 from the side showing its operation with a first pair of capacitive sensing plates or electrodes 44*a* and 44*b* for first or upper chamber 110*a* and a second or lower pair of capacitive sensing plates or electrodes 46*a* and 46*b* for second or lower chamber 110*b*. In the illustrated embodiment, sensing plates or electrodes 44*a* and 46*a* of each sensor pair located along actuation surface 24 are active capacitor plates or electrodes and connect electrically to a signal line 48*a* leading to a capacitance sensing circuit 60 of a control unit 50. Sensing plates or electrodes 44*b* and 46*b* of each sensor pair located along door 26 are ground capacitor plates or electrodes and connect electrically to a ground line 48*b* leading to a ground within door 26, which communicates electrically with the ground of housing 22. Active plates or electrodes 44*a* and 46*a* of each sensor pair abut against capacitive sensing portions 116*s* of the rigid plastic wall 116 of upper and lower chambers 110*a* and 110*b* respectively. Ground plates or electrodes 44*a* and 46*a* of each sensor pair are parallel to and directly oppose active plates or electrodes 44*a* and 46*a*. Ground plates or electrodes 44*a* and 46*a* abut against flexible (or rigid) plastic sheet 112 that extends along respective upper and lower chambers 110*a* and 110*b*. In an alternative embodiment, ground plates or electrodes 44*a* and 46*a* are merged into a single ground plate or electrode.

In general, the capacitance between (i) plates or electrodes 44*a* and 44*b* and (ii) plates or electrodes 46*a* and 46*b* is calculated using the equation:

$$C=(\varepsilon_r \times \varepsilon_0 \times A)/d, \text{ wherein}$$

$\varepsilon_r$ is the dielectric constant of the material between the plates or electrodes, $\varepsilon_0$ is the permittivity of free space ($8.85 \times 10^{-12}$ F/m), A is the area of the plates or electrodes, and d (shown in FIG. 4) is the separation between the plates or electrodes (in meters). As illustrated by Table 1, air and water/dialysis fluid have very different dielectric constants.

TABLE 1

| dielectric constants: | |
|---|---|
| water | 80 |
| air | 1 |
| metal | infinite |
| paper | 3.7 |
| acrylic | 2 to 5 |

As the liquid level rises or falls between (i) plates or electrodes 44*a* and 44*b* and (ii) plates or electrodes 46*a* and 46*b*, the capacitance between the plates changes.

FIG. 4 illustrates (i) plates or electrodes 44*a* and 44*b* abutting directly against capacitive sensing portions 116*s* of rigid plastic wall 116 and plastic sheet 112, respectively, and (ii) plates or electrodes 46*a* and 46*b* abutting directly against capacitive sensing portions 116*s* of rigid plastic wall 116 and plastic sheet 112, respectively. It is expressly contemplated to provide the direct abutting illustrated in FIG. 4. Table 1 shows however that plastic, such as acrylic, has a very low dielectric compared to that of water or dialysis fluid. The plastic walls of rigid plastic manifold 110 therefore do not adversely affect the performance of the capacitive sensors. Likewise, performance is not adversely effected if plates or electrodes 44*a* and 44*b* and plates or electrodes 46*a* and 46*b* are abutted instead inside thin plastic walls provided by actuation surface 24 and door 26, wherein the thin plastic walls instead abut rigid plastic manifold 110. This latter configuration may be desired to protect the metal plates or electrodes 44*a*, 44*b*, 46*a* and 46*b*.

Signal lines 48*a* in FIG. 4 extend to capacitance sensing circuit 60 of a control unit 50. Control unit 50 (also illustrated in FIG. 1) includes one or more processor 52, one or more memory 54 and a video controller 56 that controls a user interface 58, such as a touch screen user interface. User interface 58 may alternatively or additionally be a remote user interface, e.g., via a tablet or smartphone. Control unit 50 also includes capacitance sensing circuits 60 that each receives signals along a signal line 48 from one of the capacitive plate pairs. Control unit 50 is programmed to use the signals to look for air during treatment and to run any one or more of the calibration procedures discussed here. Control unit 50 receives signals from other sensors, such as (i) pressure sensors via holes and pressure transmission membranes 118a and 118b and/or pressure sensor 38 to control patient pumping pressure and other pumping pressures discussed above via the control of current to peristaltic pump motor 32, (ii) one or more temperature sensor 42 to control dialysis fluid heater 40 to heat fresh dialysis fluid to body temperature, e.g., 37° C., and (iii) possibly additional air sensors 36.

Control unit 50 may also include a transceiver and a wired or wireless connection to a network (not illustrated), e.g., the internet, for sending treatment data to and receiving prescription instructions/changes from a doctor's or clinician's server interfacing with a doctor's or clinician's computer. The data sent to the doctor's or clinician's computer may be analyzed and/or converted to, or used to form, other data useful for analysis. Such data conversion is performed alternatively at control unit 50.

Figure 5:
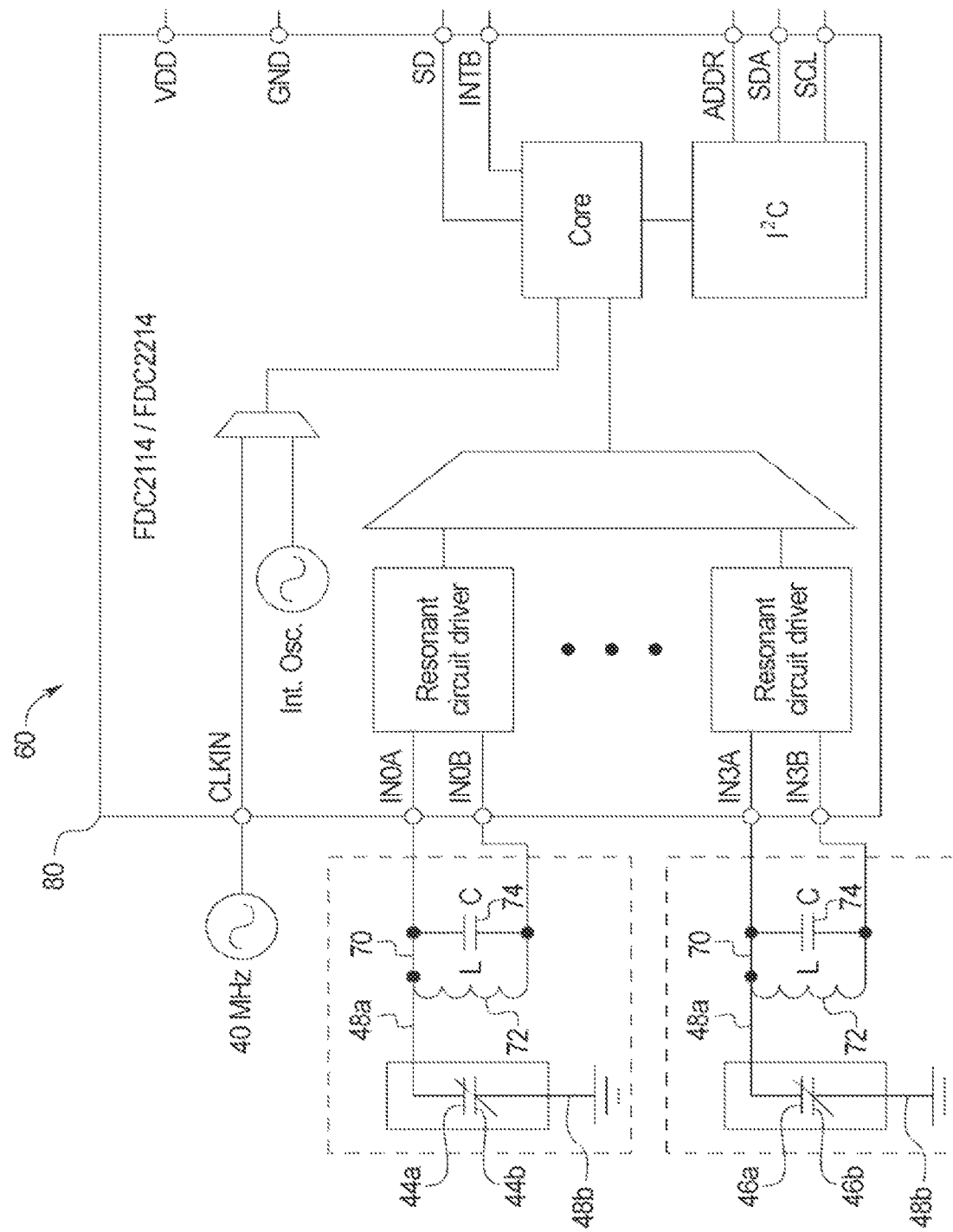
FIG. 5 is a schematic diagram illustrating one embodiment of a capacitance sensor circuit of the present disclosure.

FIG. 5 illustrates one embodiment of capacitance sensor circuit 60, which in the illustrated encompasses the capacitive sensors of both upper chamber 110a and lower chamber 110b. Capacitance sensor circuit 60 includes signal line 48a leading from active capacitor electrode or plate 44a, signal line 48a leading from active capacitor electrode or plate 46a, ground line 48b leading from ground electrode or plate 44b, and ground line 48b leading from ground electrode or plate 46b, as described above in connection with FIG. 4. Signal lines 48a leading from the active capacitor electrode or plate each lead to an L-C subcircuit 70.

The L-C subcircuits 70 are used by an FDC2214 integrated circuit 80, forming capacitance sensor circuit 60. L-C subcircuits 70 each include an inductor 72 ("L") and a capacitor 74 ("C"). A corresponding L-C oscillation frequency $f_0$ depends on total inductance L and total capacitance C according to the following equation:

$$f_0 = \frac{1}{2\pi\sqrt{LC}}$$

The values of L and C are chosen to provide a desirable range of oscillation frequencies. As the liquid level changes between active plates 44a, 46a and ground plates 44b, 46b, the capacitance between the plates will change. The change in capacitance results in different resonant frequencies $f_0$, which are measured by FDC2214 integrated circuit 80. L-C subcircuits 70 set the range of resonant frequencies $f_0$ measured. From the frequencies $f_0$ measured by FDC2214 integrated circuit 80, one or more processor 52 and one or more memory 54 of control unit 50 calculate the capacitance and the corresponding liquid level within upper chamber 110a and lower chamber 110b.

L-C subcircuits 70 provide a number of advantages. L-C subcircuits provide excellent immunity to electromagnetic interference ("EMI"). L-C subcircuits 70 also allow the operating frequency $f_0$ to be shifted if needed to avoid noise source interference.

In addition to the detection of air, the APD system 10 of the present disclosure uses capacitive sensing, including capacitance sensor circuit 60 and control unit to calibrate peristaltic pump actuator 30, which is performed in one embodiment when enough air builds in the upper chamber 110a that an air purge to drain needs to be performed. Here, control unit 50 causes peristaltic pump actuator 30 as viewed in FIGS. 1 and 3 to rotate in a counterclockwise direction to pull fresh or used dialysis fluid from lower chamber 110b into upper chamber 110a of rigid plastic manifold 110, to purge air to drain 126a. Control unit 50 uses a capacitance sensor circuit 60 with upper capacitive sensing plates or electrodes 44a and 44b to determine a volume of fresh or used dialysis fluid delivered to upper chamber 110a and counts the number of pump strokes, including any partial pump stroke. Regarding partial pump strokes, it is contemplated to provide an encoder for use with peristaltic pump motor 32, wherein the encoder allows a full revolution of 360° to be divided into many fractions of a rotation, e.g., into 5919 fractions. Control unit 50 then divides the volume determined via capacitance sensor circuit 60 by the number of pump strokes to determine the volume per revolution in the counterclockwise direction. Control unit 50 uses that volume per revolution going forward (multiplying by counted revolutions including partial revolutions) when rotating the peristaltic pump actuator in the counterclockwise direction, e.g., for patient draining volume and flowrate determination. Lower capacitive sensor plates 46a and 46b may be used additionally (for confirmation) or alternatively to detect how much fluid leaves lower chamber 110b over the known amount of peristatic pump strokes or revolutions, so that the volume per revolution of the peristaltic pump in the same counterclockwise direction may be calculated and used. Lower capacitive sensor plates 46a and 46b and associated circuitry also form the primary sensing structure for air detection and mitigation during treatment.

Control unit 50 then causes peristaltic pump actuator 30 to rotate in the opposite, clockwise direction as viewed in FIGS. 1 to 3 to push fluid from upper chamber 110a into lower chamber 110b of rigid plastic manifold 110. Control unit 50 uses a capacitance sensor circuit 60 with upper capacitive sensor plates 44a and 44b to detect how much fluid leaves upper chamber 110a over a known amount of peristatic pump strokes or revolutions, including partial revolutions, so that the current volume/stroke of the peristaltic pump in the opposite, clockwise direction can be calculated and used going forward (multiplying by counted revolutions including partial revolutions) when rotating the peristaltic pump actuator in the clockwise direction, e.g., for patient filling. Lower capacitive sensing plates or electrodes 46a and 46b may be used additionally (for confirmation) or alternatively to detect how much fluid enters lower chamber 110b over the known amount of peristatic pump strokes or revolutions, so that the volume per revolution of the peristaltic pump in the same clockwise direction may be calculated or confirmed. Again, Lower capacitive sensing plates or electrodes 46a and 46b may be used primarily for air detection and mitigation during treatment.

Figure 6:
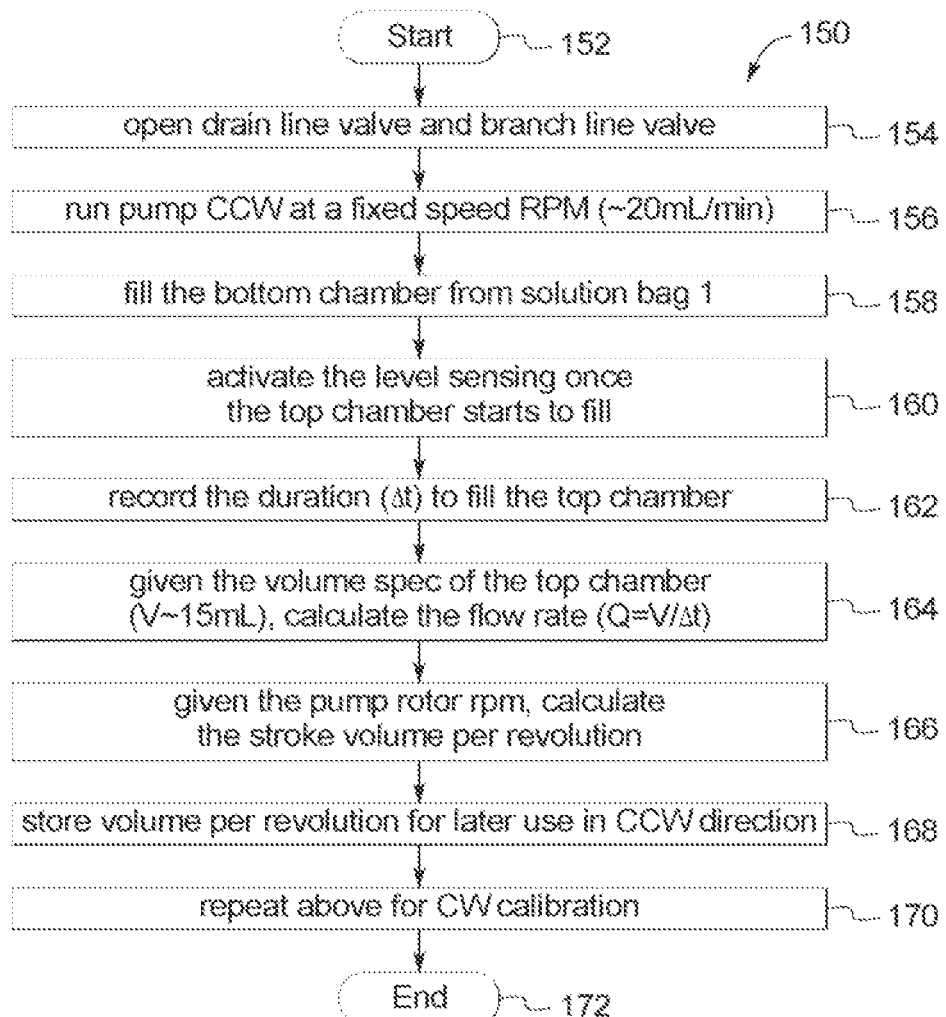
FIG. 6 is process flow diagram illustrating one embodiment of a peristaltic pump calibration procedure of the present disclosure.

In an alternative embodiment, control unit 50 runs a calibration sequence 150 according to FIG. 6 to calibrate peristaltic pump actuator 30. Calibration sequence 150 may be performed at any time when at least upper chamber 110a is empty. The volume of upper chamber 110a is known. At oval 152, calibration sequence 150 begins. At block 154, control unit 50 causes drain valve drain line valve 34a and branch line valve 34c to open, while all other valves remain closed.

At block 156, control unit 50 causes peristaltic pump actuator 30 as viewed in FIGS. 1 and 3 to run in a counterclockwise direction to pump fresh dialysis fluid at a known revolutions per minute ("rpm") for motor 32 (e.g., to attempt to pump at 20 ml/min). At block 158, the counterclockwise movement of pump actuator 30 pulls fresh dialysis fluid from dialysis fluid container 126b into lower chamber 110b via branch line 124c.

At block 160, control unit 50 monitors upper capacitive sensing plates or electrodes 46a and 46b and their capacitance sensor circuit 60 once dialysis fluid enters upper chamber 110a. At block 162, control unit 50 while monitoring the upper capacitance sensor also records the time duration needed to fill upper chamber 110a. At block 164, control unit 50 calculates the flowrate by dividing the known volume of upper chamber 110a by the time duration just recorded. At block 166, control unit 50 calculates the volume per revolution in the counterclockwise direction by dividing the just calculated flowrate by the known rpm. At block 168, control unit 50 is programmed to use the just calculated volume per revolution (multiplying by counted revolutions including partial revolutions) going forward when pumping in the counterclockwise direction, e.g., for a patient drain.

At block 170, the above steps of calibration sequence 150 are then be repeated in the opposite, clockwise direction by draining upper chamber 110a and measuring the time duration needed to do so. The rpm or motor 32 and the volume of chamber 110a are again known, so that control unit 50 may calculate the volume per revolution in the clockwise direction by dividing the volume of chamber 110a by the measured time duration for draining and then dividing the resulting flowrate by the known rpm. Control unit 50 then uses the just calculated volume per revolution (multiplying by counted revolutions including partial revolutions) going forward when pumping in the clockwise direction, e.g., for a patient fill. At oval 172, method 150 ends.

Figure 7:
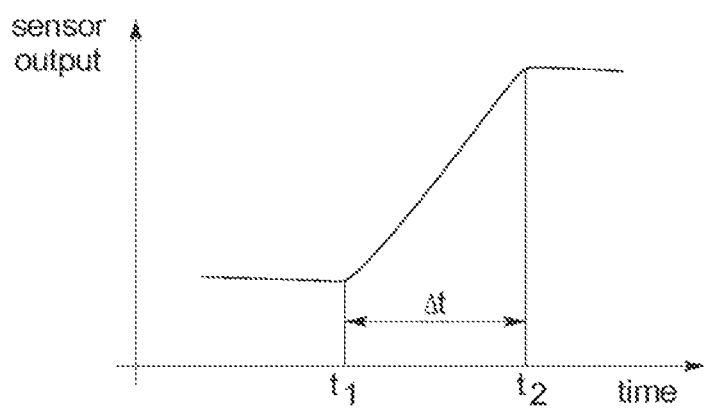
FIG. 7 is a plot illustrating capacitance sensor output over time, wherein the illustrated duration of time Δt is used in the calibration procedure of FIG. 6.

Referring now to FIG. 7, a plot showing capacitance sensor output over time is illustrated, wherein the illustrated duration of time $\Delta t$ is used in the calibration procedure of FIG. 6 and sequence 150. Time $t_1$ corresponds to block 160, wherein upper capacitive sensing plates or electrodes 46a and 46b and their capacitance sensor circuit 60 are monitored once dialysis fluid enters upper chamber 110a. Time $t_2$ corresponds to the end of the capacitance measuring at block 162, wherein upper chamber 110a becomes full and the capacitance no longer increases. The difference between $t_2$ and $t_1$ is $\Delta t$, which is used in block 164 to calculate the average flowrate while filling first or upper chamber 110a.

Figure 8:
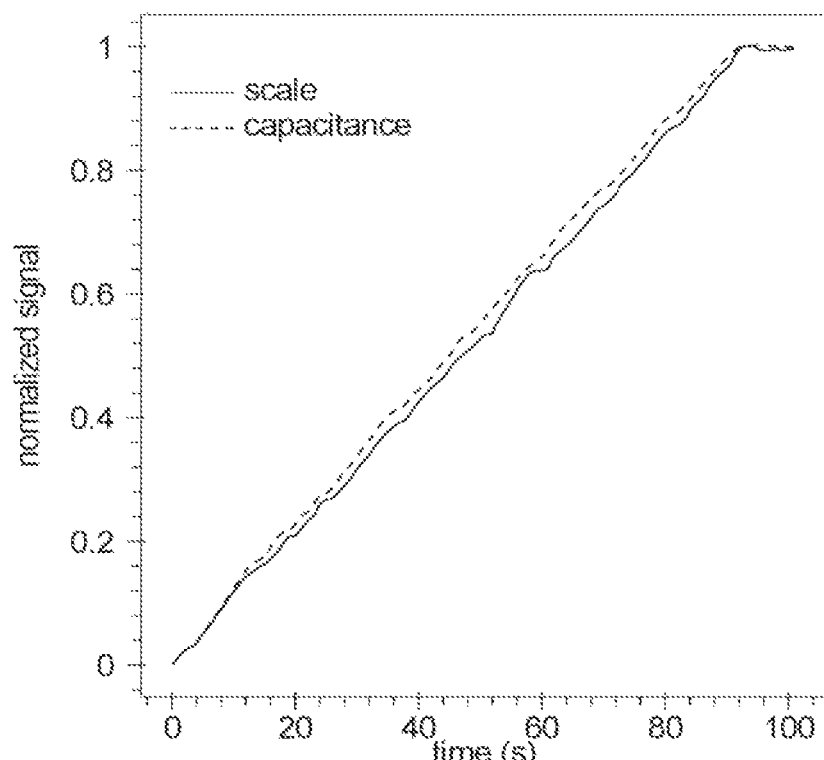
FIG. 8 is a plot comparing an output of a capacitance sensor of the present disclosure against a weight scale output for the same fluid fill.

Referring now to FIG. 8, a plot comparing capacitance sensor output against a weight scale output for a same fluid fill is illustrated. In FIG. 8, the output of upper capacitive sensing plates or electrodes 44a and 44b or lower capacitive sensing plates or electrodes 46a and 46b operating with their corresponding capacitance sensor circuit 60, while their respective chamber 110a or 110b is filled is plotted against the output of a weight scale weighing the same filling of the same chamber. Both the capacitance sensor output and the weight scale output are normalized to [0-1]. FIG. 8 demonstrates a clear match between the two outputs, showing that the capacitance sensors of system 10 of the present disclosure are accurate.

Figure 9:
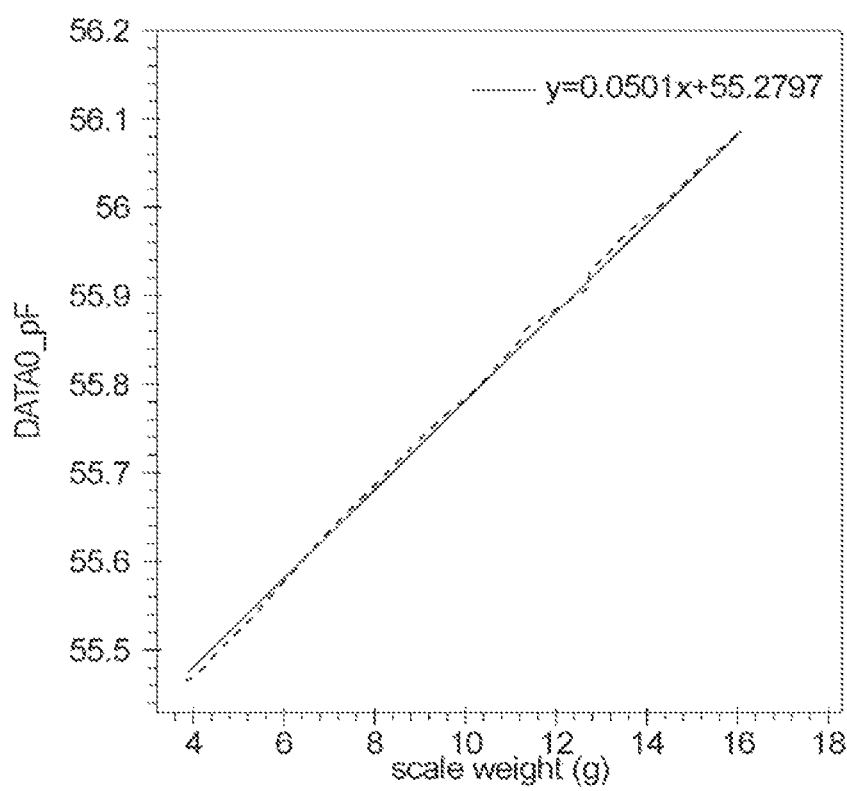
FIG. 9 is a plot showing an equation stored in software for converting an output of a capacitance sensor of the present disclosure to a dialysis fluid weight.

Referring now to FIG. 9, a plot showing an equation stored in software at one or more memory 54 for converting an output of a capacitance sensor of the present disclosure to a weight of fluid is illustrated. Here, the weight of the dialysis fluid (y) inside of one of chambers 110a or 110b is determined from a measured signal value (x) from upper capacitive sensing plates or electrodes 44a and 44b or lower capacitive sensing plates or electrodes 46a and 46b operating with their respective capacitance sensor circuit 60 according to the following equation stored in software: $y = 0.0501x + 55.2797$.

It should be appreciated that for any calibration embodiment described herein, the calibration procedure may be run at a flowrate that is lower than the flowrates used typically during treatment. For example, the calibration procedures may be run at 20 ml/min or other lower flowrate known to produce accurate capacitance readings. Filling and draining flowrates are typically in the range of 200 ml/min to 250 ml/min. It is also contemplated for control unit 50 of system 10 to run pressure or flow profiles for at least one of a patient fill and patient drain, which may begin at lower pressures and flowrates, ramp up to higher pressures and flowrates during the middle of the fill or drain, and ramp down to lower pressures and flowrates at the end of the fill or drain. The beginning and end of the patient fills and drains are when the patient is most sensitive. Patient fill pressures may for example be controlled to be less than 1.5 psig at the beginning and/or end, e.g., for at least one of first and last 10%, of the patient fill, and then ramp up to as high as 9.5 psig during the middle 80% to 90% of the fill. Flowrates may correspondingly start and/or end at around 60 ml/min and then ramp up to around 200 ml/min to 250 ml/min. Patient drain pressures may for example be controlled to be less than −1.5 psig at the beginning and/or end, e.g., for at least one of first and last 10%, of the patient drain, and then ramp up to as high as −3.0 psig during the middle 80% to 90% of the drain.

In one embodiment, control unit 50 of system 10 performs an initial calibration of peristaltic pump actuator 30 and peristaltic pumping tube 124gh in both counterclockwise and clockwise directions according to any of the embodiments described herein. Next, without knowing if the patient is full of effluent from a prior treatment or not, control unit 50 of system 10 assumes that the patient is full of effluent and automatically attempts an initial drain, e.g., at a low pressure and flowrate. If the patient is not full of effluent, control unit 50 of system 10 detects same immediately either by sensing a high resistance pressure caused by the empty patient catheter or by detecting air in lower chamber 110b via the capacitive sensing. Control unit 50 then proceeds to a patient fill. It is contemplated to recalibrate peristaltic pump actuator 30 and peristaltic pumping tube 124gh in both counterclockwise and clockwise directions during each patient dwell of a treatment.

Figure 10:
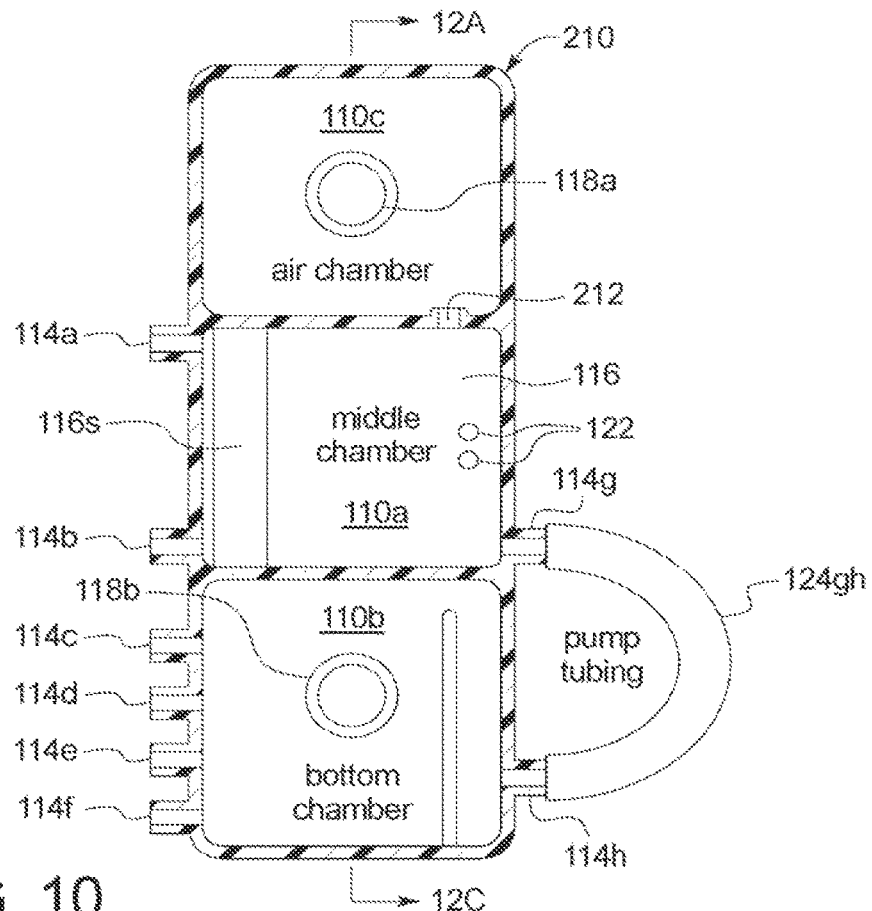
FIG. 10 is a front view illustrating one alternative disposable rigid plastic manifold of the APD system of the present disclosure.

Referring now to FIG. 10, an alternative rigid plastic manifold 210 for use with system 10 is illustrated. Rigid plastic manifold 210 may be made of any of the materials and processes described herein and includes many of the same structure, functionality and alternatives discussed above for rigid plastic manifold 110, wherein those structures are numbered the same and not repeated here. For example, rigid plastic manifold 210 includes first chamber 110a and second chamber 110b. Additionally, manifold 210 includes a third chamber 110c that is located, e.g., molded, on top of the former upper chamber 110a, making it now the middle chamber of third chamber manifold 210. One or more aperture 212 is formed between first or middle chamber 110a and third or upper chamber 110c, however, it is contemplated that fluid does not flow from middle chamber 110a to the upper, third chamber 110c. Instead, upper chamber 110c is provided to supply air to middle chamber 110a during a calibration sequence discussed below.

FIG. 10 illustrates that it is contemplated to move pressure sensing hole and accompanying pressure sensing membrane 118a from upper chamber 110a of two chamber manifold 110 to upper chamber 110c of three chamber manifold 210. In an alternative embodiment, pressure sensing hole and accompanying pressure sensing membrane 118a remains in first chamber 110a and a third pressure sensing hole and accompanying pressure sensing membrane is added to upper chamber 110c of the three chamber manifold 210.

In an embodiment, rigid manifold 210 provides capacitive sensing portions 116s along rigid plastic wall 116, which operate with upper capacitive sensing plates or electrodes 44a and 44b and lower capacitive sensing plates or electrodes 46a and 46b and their capacitance sensor circuit 60. Lower capacitive sensing plates or electrodes 46a and 46b my again be provided mainly for air detection and mitigation during treatment. In an alternative embodiment for both rigid manifolds 110 and 210 of system 10, only upper capacitive sensing plates or electrodes 44a and 44b for first chamber 110a are provided. Here, the lower capacitive sensor for chamber 110b is not provided. In either case for manifold 210, added upper chamber 110c is not intended to hold fluid and does not operate with capacitive sensing plates or electrodes accordingly in one embodiment.

Figure 11:
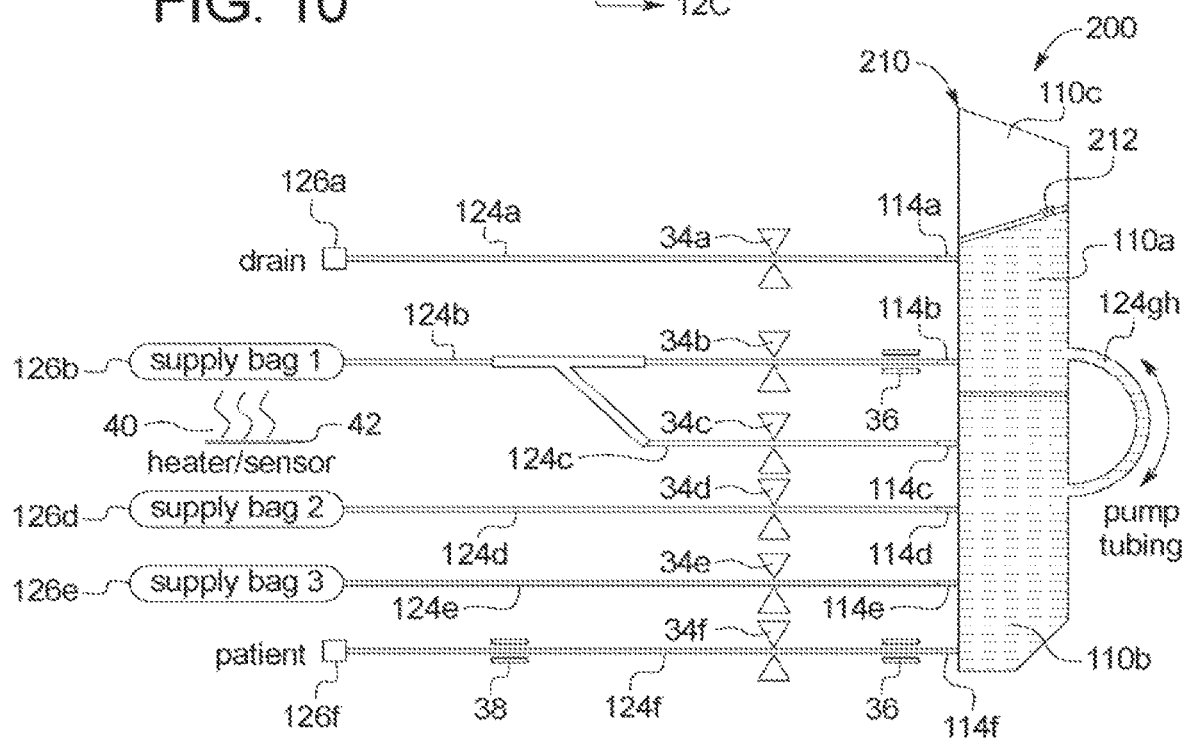
FIG. 11 is a front view illustrating one embodiment of a flow regime for the alternative manifold of FIG. 10.

FIG. 11 illustrates alternative manifold assembly 200 of system 10 using alternative rigid manifold 210. Here again, the tubing and containers of manifold assembly 200 may be made of any of the materials and processes described herein and includes many of the same structure, functionality and alternatives discussed above for manifold assembly 100, wherein those structures are numbered the same and not repeated here. The operation and control of valves 34a to 34f, peristaltic pump actuator 30 and heater 40 for (i) pumping fresh dialysis fluid to heater 40 for heating, (ii) pumping heated, fresh dialysis fluid to the patient, (iii) pumping used dialysis fluid to drain, (iv) removing leftover fresh dialysis fluid from dialysis fluid container 126b to drain, and (v) removing air to drain is performed for system 10 using alternative manifold assembly 200 in the same manner as described above for system 10 using manifold assembly 100.

Figures 12A, 12B, 12C:
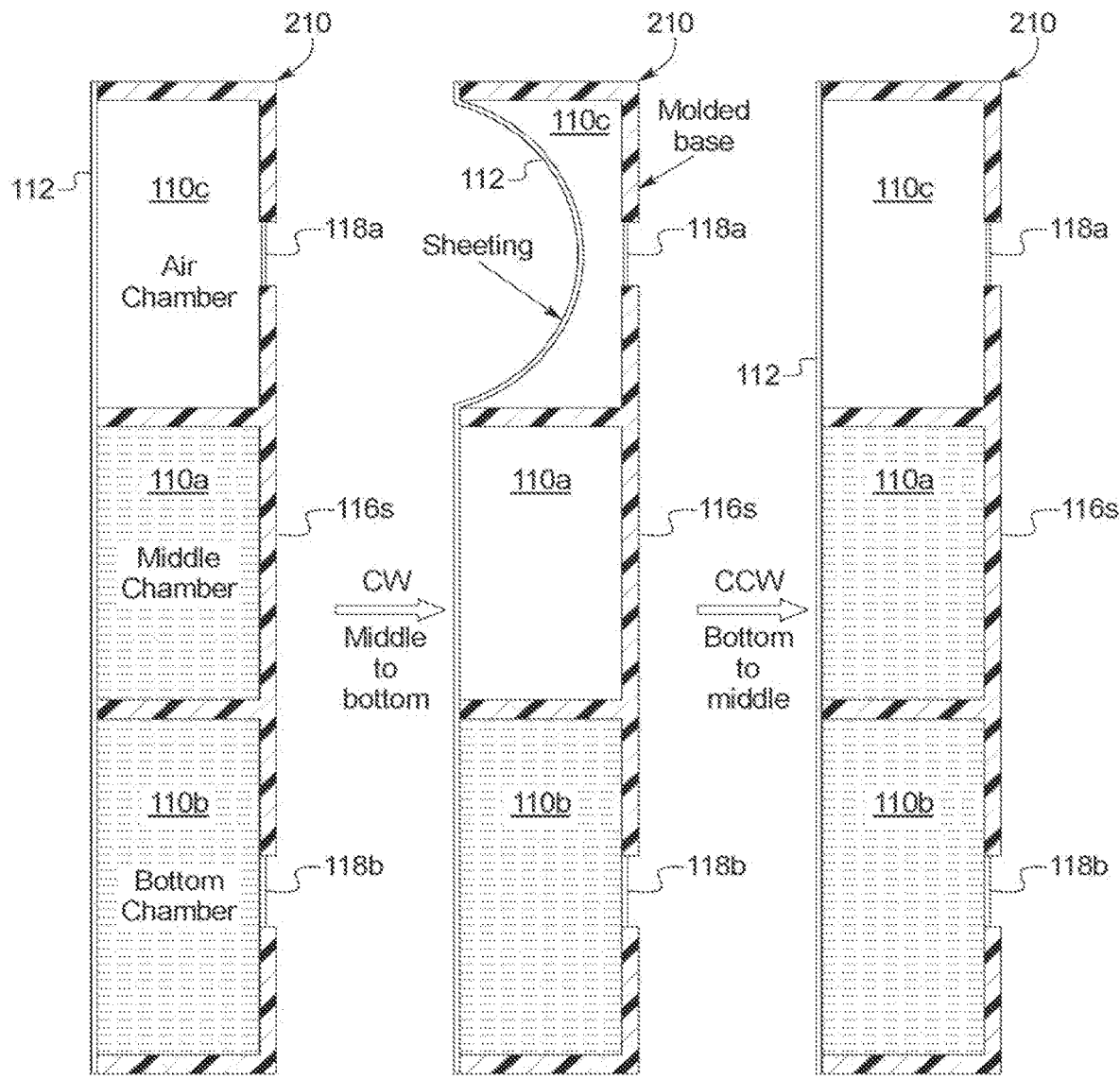
FIGS. 12A to 12C are side views taken along line 12A-12C of the alternative disposable rigid plastic manifold of FIG. 11 illustrating one possible peristaltic pump calibration procedure using the manifold.

FIGS. 12A to 12C illustrate one possible peristaltic pump calibration procedure performed under control of control unit 50 using alternative rigid manifold 210 and manifold assembly 200. Third, upper chamber 110c is added to help perform the calibration procedure. In a first step of the calibration procedure as illustrated in FIG. 12A, fresh dialysis fluid is pulled from one of the dialysis fluid containers 126b, 126d or 126e to prime middle chamber 110a and lower chambers 110b completely, as determined using the upper capacitance sensor alone or in combination with the lower capacitance sensor, so that all air is pushed to drain.

In a next step illustrated in FIG. 12B, pinch valve 34c for branch line 124c leading from first dialysis fluid container 126b to lower chamber 110b is opened, and peristaltic pump actuator 30 is actuated at a known revolutions per minute ("rpm") in a first direction (clockwise in FIG. 11) so as to move dialysis fluid from middle chamber 110a to lower chamber 110b until the middle chamber is completely empty as measured by capacitive sensing plates or electrodes 44a and 44b and capacitance sensor circuit 60, wherein (i) dialysis fluid in lower chamber 110b migrates through open branch line 124c into first dialysis fluid container 126b, (ii) air from the third, upper chamber 110c is pulled into middle chamber 110a, and (iii) flexible (or rigid) sheet 112 extended to cover third chamber 110c bows inward into the upper chamber to compensate for the air that moves from upper chamber 110c into middle chamber 110b. The volume of the middle chamber (Vu) is known and the time duration (Δt) needed to fully drain middle chamber 110a is measured at control unit 50. Knowing those two parameters and the rpm of peristaltic pump actuator 30 actuated in the chamber draining direction (clockwise) allows the stroke volume per revolution in the chamber draining direction to be calculated, namely, to be equal to $V_m/\Delta t/rpm$, e.g., in milliliters ("ml")/rpm.

In a next step illustrated in FIG. 12C, wherein pinch valve 34c for branch line 124c leading from first dialysis fluid container 126b to lower chamber 110b remains open, peristaltic pump actuator 30 is actuated at a known revolutions per minute ("rpm") in a second direction (counterclockwise in FIG. 11) so as to move dialysis fluid from lower chamber 110b to middle chamber 110a until the middle chamber is completely full as measured by capacitive sensing plates or electrodes 44a and 44b and capacitance sensor circuit 60, wherein (i) dialysis fluid from first dialysis fluid container 126b flows through open branch line 124c into the lower chamber 110b and from the lower chamber into middle chamber 110a, (ii) air is pushed from middle chamber 110a into upper chamber 110c, and (iii) flexible (or rigid) sheet 112 straightens within upper chamber 110c due to the air being pushed into the upper chamber by the dialysis fluid entering middle chamber 110a. The volume of middle chamber 110a ($V_m$) is known and the time (Δt) needed to fully fill the middle chamber is measured at control unit 50. Knowing those two parameters and the rpm of peristaltic pump actuator 30 actuated in the chamber filling direction (counterclockwise) allows the stroke volume per revolution in the chamber filling direction to be calculated, namely, to be equal to $V_m/\Delta t/rpm$, e.g., in ml/rev.

Control unit 50 is configured to use the results of the peristaltic pump calibration procedures discussed in connection with FIGS. 12A to 12C and in the other embodiments going forward to determine how much fresh PD fluid is delivered to the patient and how much used PD fluid is removed from the patient. That is, knowing the latest volume per revolution, control unit 50 thereafter counts the number of revolutions (including partial revolutions) over a patient fill or patient drain and multiples that number times the latest volume per revolution to determine the volume of fluid filled to or drained from the patient. It should be appreciated that volume per revolution could instead be weight per revolution (grams/rev), wherein the weight of fresh or used dialysis fluid within a particular chamber of the manifold is known.

Figures 13A, 13B:
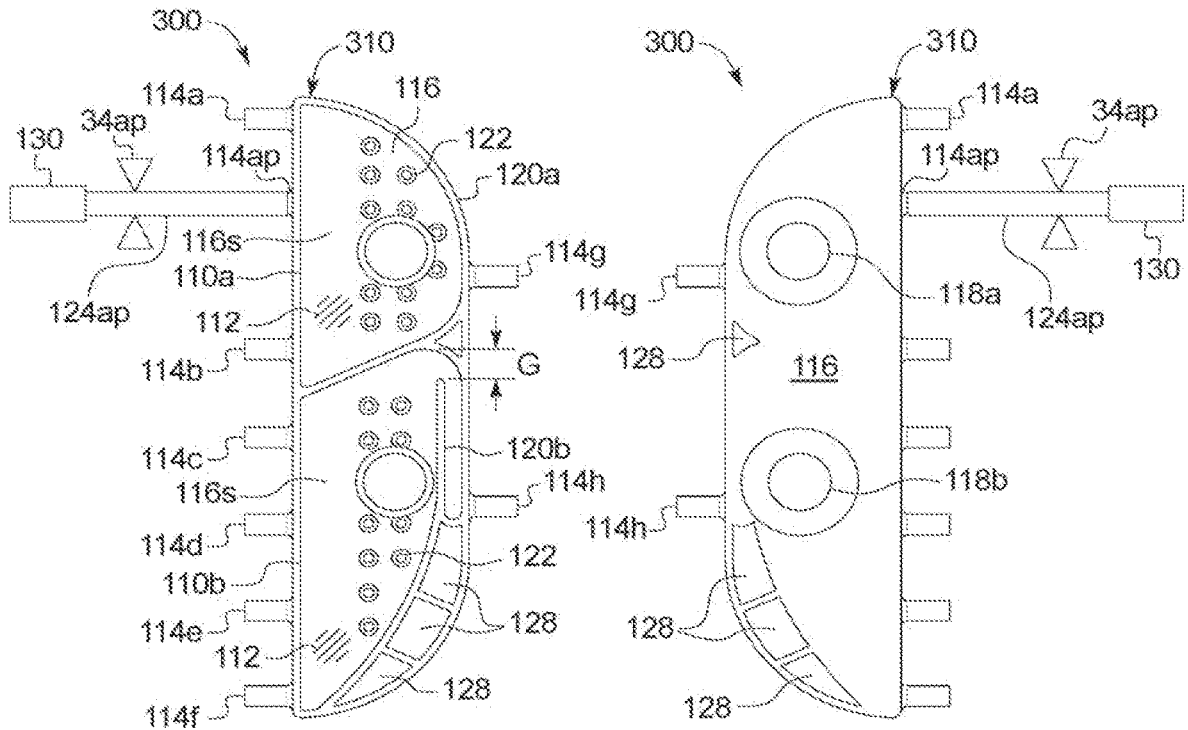
FIGS. 13A to 13C illustrate one embodiment for providing an unlimited source of air to the disposable rigid plastic manifold of the present disclosure.
Figure 13C:
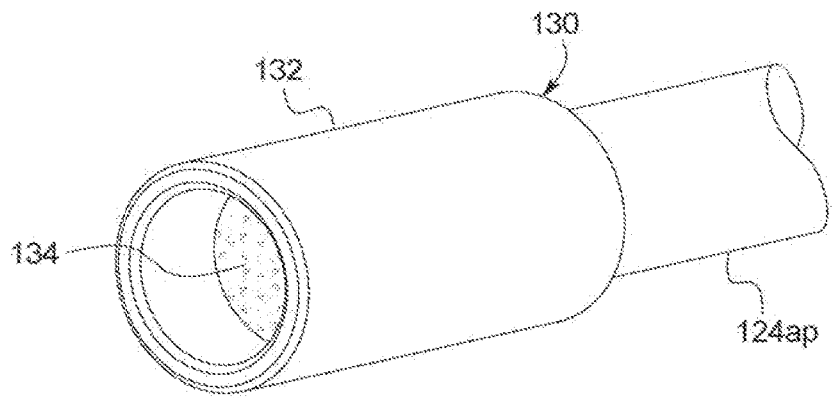

Manifold assembly 100 and alternative manifold assembly 200 in the illustrated embodiments are closed with respect to outside ambient air and rely on air generated or existing within rigid plastic manifolds 110 and 210 to perform the peristaltic pump accuracy calibration sequences discussed herein. Referring now to FIGS. 13A to 13C, a first unlimited air manifold 310 for use with alternative manifold assembly 300 of alternative system 10 is illustrated. Rigid plastic manifold 310 may be made of any of the materials and processes described herein and includes many of the same structures, functionality and alternatives discussed above for rigid plastic manifold 110, wherein those structures are numbered the same and may not be repeated here. For example, rigid plastic manifold 310 includes first chamber 110a and second chamber 110b, each covered via a flexible (or rigid) plastic sheet 112. Rigid plastic manifold 310 also includes drain port 114a, first heater line/first dialysis fluid container port 114b, bypass or branch line port 114c, second dialysis fluid container port 114d, third dialysis fluid container port 114e, patient line port 114f and peristaltic pump ports 114g and 114h. Rigid plastic manifold 310 further includes rigid plastic wall 116 having sensing portions 116s, and walls 120a and 120b provided to help guide dialysis fluid and air flow. Rigid plastic manifold 310 also includes pegs 122 extending inwardly from the rigid plastic wall 116, which prevent flexible plastic sheet 112 from collapsing under negative pressure. In the instance in which plastic sheet 112 is instead a rigid plastic lid, pegs 122 are not needed or provided.

In the illustrated embodiment, rigid plastic manifold 310 of alternative manifold assembly 300 additionally includes an air port 114ap positioned and arranged to allow filtered, ambient air to be pulled into upper chamber 110a. An air port line or tube 124p is made of any of the materials discussed herein and is sealed to air port 114ap via any technique described herein, e.g., ultrasonically, via heat seal or adhesively. Air port line or tube 124ap may be short, e.g., long enough to interact with a pinch valve. A filter connector 130 is likewise is made of any of the materials discussed herein and is sealed to the end of air port line or tube 124ap via any technique described herein. Filter connector 130 in the illustrated embodiment includes a filter housing 132, which houses a hydrophobic filter 134. Hydrophobic filter 134 is configured to allow air but not liquid, e.g., dialysis fluid, to pass through housing 132. Hydrophobic filter 134 also filters and purifies ambient air entering rigid plastic manifold 310 via air port line or tube 124ap, so that the air may interface with sterilized dialysis fluid.

Any of the manifolds 110, 210, 310, 410 and 510 discussed herein may include material removal openings 128 to reduce disposable cost.

FIGS. 13A and 13B illustrate that APD cycler 20 provides an air port valve 34ap that operates with air port line or tube 124ap. Air port valve 34ap, like the other valves, is under control of control unit 50 and may be an electrically actuated solenoid pinch valve, which opens in a fail safe manner upon being energized. Pinch valve 34ap is typically closed during treatment to prevent air from entering manifold assembly 300 and fresh or used dialysis fluid from reaching filter connector 130 and hydrophobic filter 134. Control unit 50 opens pinch valve 34ap and runs peristaltic pump head or actuator 30 in a clockwise direction to pull air into upper chamber 110a at any time it is desired to calibrate the peristaltic pump actuator. In an embodiment, control unit 50 closes all other pinch valves 34a to 34f when pulling air into manifold assembly 300.

The above structure allows for an unlimited supply of air to be provided at any desired time. Volumetric calibration may therefore be performed at any time prior to the start of therapy and, for example, during peritoneal dialysis treatment dwells. Manifold assembly 300 allows for multiple calibration attempts (e.g., for averaging), at multiple pump actuator speeds, and in both pump directions. If an initial calibration sequence fails, for example, manifold assembly 300 allows for an immediate subsequent calibration sequence with the same disposable, which reduces treatment delays and disposable scrap.

Referring now to FIGS. 14A and 14B, a second unlimited air manifold 410 for use with an alternative manifold assembly 400 of alternative system 10 is illustrated. Rigid plastic manifold 410 may be made of any of the materials and processes described herein and includes many of the same structures, functionality and alternatives discussed above for rigid plastic manifold 110, wherein those structures are numbered the same and may not be repeated here. For example, rigid plastic manifold 410 includes first chamber 110a and second chamber 110b, each covered via a flexible (or rigid) plastic sheet 112. Rigid plastic manifold 410 also includes drain port 114a, first heater line/first dialysis fluid container port 114b, bypass or branch line port 114c, second dialysis fluid container port 114d, third dialysis fluid container port 114e, patient line port 114f and peristaltic pump ports 114g and 114h. Rigid plastic manifold 410 further includes rigid plastic wall 116 having sensing portions 116s, and walls 120a and 120b provided to help guide fluid and air flow. Rigid plastic manifold 410 also includes pegs 122 extending inwardly from rigid plastic wall 116, which prevent flexible plastic sheet 112 from collapsing under negative pressure. In the instance in which plastic sheet 112 is instead a rigid plastic lid, pegs 122 are not needed or provided.

In the illustrated embodiment, second unlimited air manifold 410 of alternative manifold assembly 400 of system 10 additionally includes a dedicated air port 114ap located on back wall 116 of the manifold. Dedicated air port 114ap is routed to upper chamber 110a of manifold 410 via a molded air pathway 412. A hydrophobic air filter 414 is attached to the back of air port 114ap. Hydrophobic filter 414 is configured to allow air to be pulled into upper chamber 110a and to prevent fresh or used dialysis fluid from escaping manifold 410 into cycler 20. Hydrophobic filter 414 also filters and purifies ambient air entering rigid plastic manifold 410, so that the air may interface with sterilized dialysis fluid.

Cycler 20 operating with manifold assembly 400 provides a seal (not illustrated), e.g., a spring closed and pneumatically opened seal, to normally seal the hydrophobic filter 414 closed. Cycler 20 provides a pneumatic pump and possibly a pneumatic supply tank to supply, e.g., negative pressure to overcome the spring force and pull the seal from hydrophobic filter 414 to expose the filter to ambient air. Cycler 20 accordingly includes at least one pneumatic valve under control of control unit 50 to open and close a pneumatic line leading to the seal. The pneumatic valve is normally closed until air is needed in rigid plastic manifold 410 for a volumetric calibration. Peristaltic pump actuator 30 is operated again in a clockwise direction to draw in air into top chamber 110a at any time and for any amount of air needed for the volumetric calibration.

Figure 15:
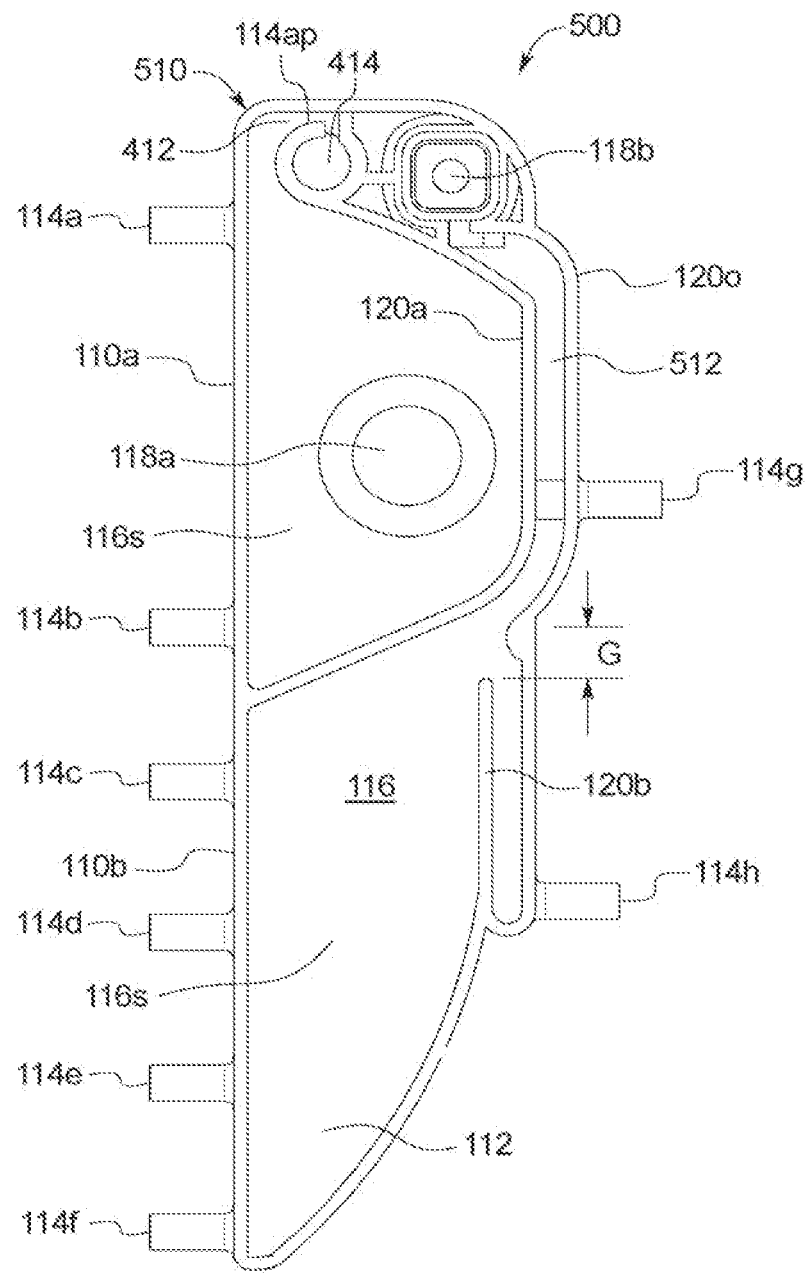
FIG. 15 illustrates a further alternative disposable rigid plastic manifold of the present disclosure having an air passage for pressure sensing.

Referring now to FIG. 15, a further alternative rigid manifold 510 for use with an alternative manifold assembly 500 of alternative system 10 is illustrated. Rigid plastic manifold 510 may be made of any of the materials and processes described herein and includes many of the same structures, functionality and alternatives discussed above for rigid plastic manifold 110, wherein those structures are numbered the same and may not be repeated here. For example, rigid plastic manifold 510 includes first chamber 110a and second chamber 110b, which in the illustrated embodiment are each covered via a rigid plastic sheet 112 (could alternatively be flexible). Rigid plastic manifold 510 also includes drain port 114a, first heater line/first dialysis fluid container port 114b, bypass or branch line port 114c, second dialysis fluid container port 114d, third dialysis fluid container port 114e, patient line port 114f and peristaltic pump ports 114g and 114h. Rigid plastic manifold 510 further includes rigid plastic wall 116 having sensing portions 116s, and walls 120a and 120b provided to help guide fluid and air flow. Rigid plastic manifold 510 does not require pegs 122 if employing a rigid front wall 112. Pegs 122 are provided if plastic wall 112 is flexible.

Rigid plastic manifold 510 also includes pressure sensing aperture 118a, such as a circular hole, formed or provided in rigid plastic wall 116 of upper chamber 110a, which is covered with a pressure sensing membrane. When manifold 510 is mounted to APD cycler 20 for operation, the pressure sensing membrane covering hole 118a abuts against a pressure transducer provided by the cycler at actuation surface 24. Rigid plastic manifold 510 further includes dedicated air port 114ap located on back wall 116 of the manifold. Dedicated air port 114ap is routed to upper chamber 110a of manifold 410 via a molded air pathway 412. Hydrophobic air filter 414 is attached to the back of air port 114ap to allow air to be pulled into upper chamber 110a and to prevent fresh or used dialysis fluid from escaping manifold 410 into cycler 20.

In the illustrated embodiment, pressure sensing aperture 118b is not provided in lower chamber 110b. Pressure sensing aperture 118b is provided instead in back wall 116 adjacent to air port 114ap. Pressure sensing aperture 118b with manifold 510 is covered by a hydrophobic filter instead of an air impermeable pressure sensing membrane. When manifold 510 is mounted to APD cycler 20 for operation, the hydrophobic filter covering hole 118b is placed in registry with a pressure transducer provided by the cycler at actuation surface 24. Pressure sensing aperture 118b and its hydrophobic filter covering are in fluid communication with lower chamber 110b via an air channel 512 located between wall 120a and an outer wall 120o of rigid plastic manifold 510. Air channel 512 leading upward to pressure sensing aperture 118b and its hydrophobic filter covering aids in the sensing of fresh or used dialysis fluid pressure delivered to or removed from the patient, respectively, by providing a direct communication with the pressure transducer and the air pressurized via the pressure of fresh or used dialysis fluid in lower chamber 118b via the hydrophobic filter. There is no dependence on the elastic properties of an air impermeable plastic membrane on the disposable to transduce the pressure signal. Here, the fresh or used dialysis fluid compresses or expands the air within channel 512, which has direct communication to the pressure transducer of the cycler via the hydrophobic filter.

As discussed above, control unit 50 in one embodiment includes a transceiver and a wired or wireless connection to a network, e.g., the internet, for sending treatment data to and receiving prescription instructions from a doctor's or clinician's server interfacing with a doctor's or clinician's computer. In particular for system 10, it is contemplated for control unit 50 to send data over the network regarding an analysis of the patient's effluent, wherein the data is used to determine the effectiveness of the patient's APD treatment. The doctor or clinician may review the data to determine if the patient's prescription should be modified, e.g., dwell times modified and/or a change in dialysis fluid formulation. The data sent from APD cycler 20, though the network to the doctor or clinician may be the same as, or akin to, data obtained from a peritoneal equilibration test ("PET").

PETs determine the mass transport characteristics associated with the patient's peritoneum. PETs help doctors and clinicians to decide whether a patient's PD treatment may be improved, e.g., using different dwell times and/or different PD fluid formulation. A full PET may take around five hours to complete and may involve a CAPD exchange for example using a 2.27% glucose solution. Samples of PD fluid and patient blood are taken at set times. It is known that classical parameters of peritoneal transport such as glucose reabsorption and creatinine transport have a direct correlation with the ionic conductivity of patient effluent. Conductivity has also been used to distinguish patients with and without ultrafiltration failure.

The capacitive sensing associated with the dual chamber manifold 110 and three chamber 210 of system 10 provide an opportunity determine the conductivity associated with both the fresh and used dialysis fluid and to use the measured and determined conductivities to develop data and send the data via a network to locations that have the need and ability to clinically analyze the data for the reasons discussed above. In particular, capacitive sensing plates or electrodes 44a and 44b and 46a and 46b and associated capacitance sensor circuits 60 provide a measure of a liquid dielectric constant from which a conductivity value can be derived.

Figure 16:
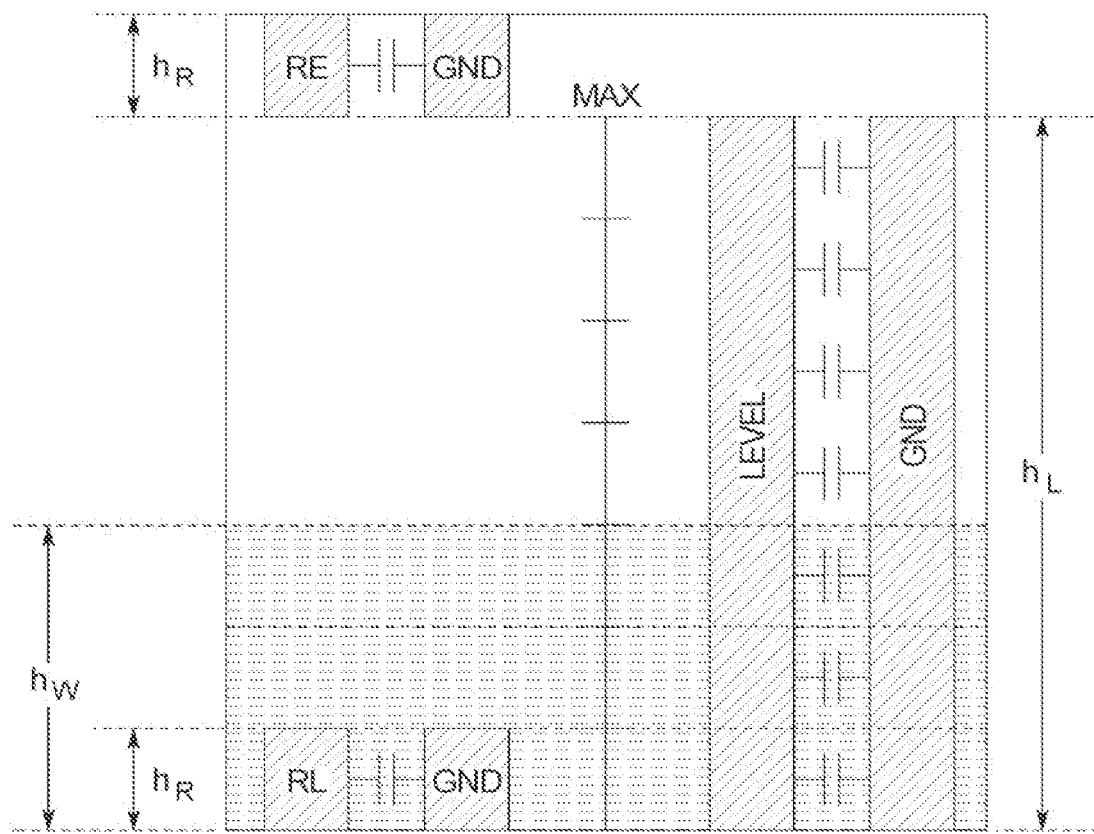
FIGS. 16 and 17 are schematic views helping to illustrate the relationship between capacitance and conductivity for a peritoneal effectiveness evaluation of the present disclosure.
Figure 17:
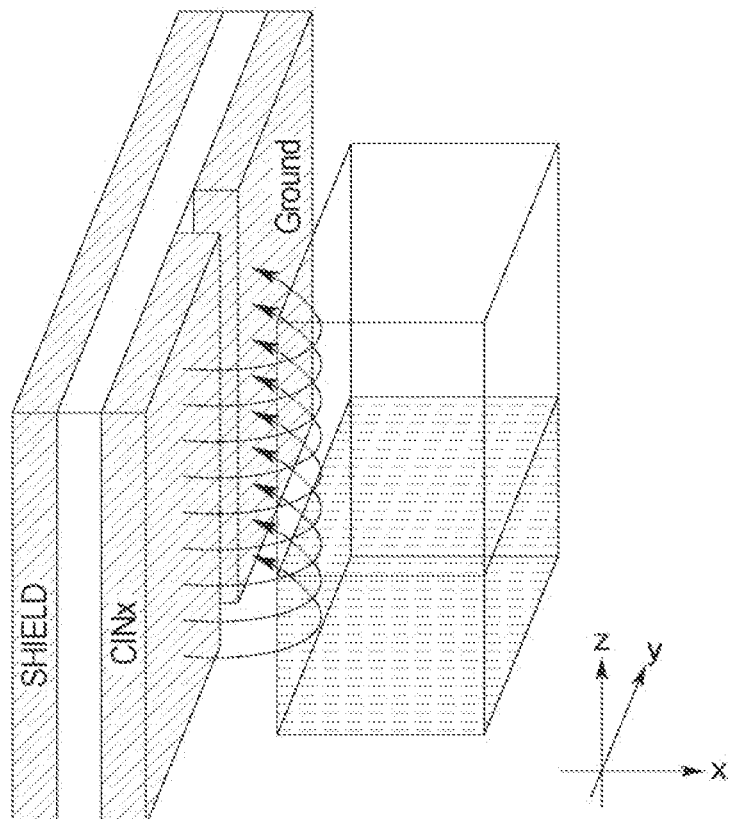

FIGS. 16 and 17 illustrate how capacitance is dependent on the dielectric properties of dialysis fluid and air in a model that represents chambers 110a and 110b. In particular, capacitance $C_{meas}$ is a function of (height of the dialysis fluid $h_W$ multiplied by the dielectric of the dialysis fluid $\varepsilon_w$) plus (maximum height of the dialysis fluid $h_L$ less $h_W$) multiplied by the dielectric of air $\varepsilon_a$.

Figure 18:
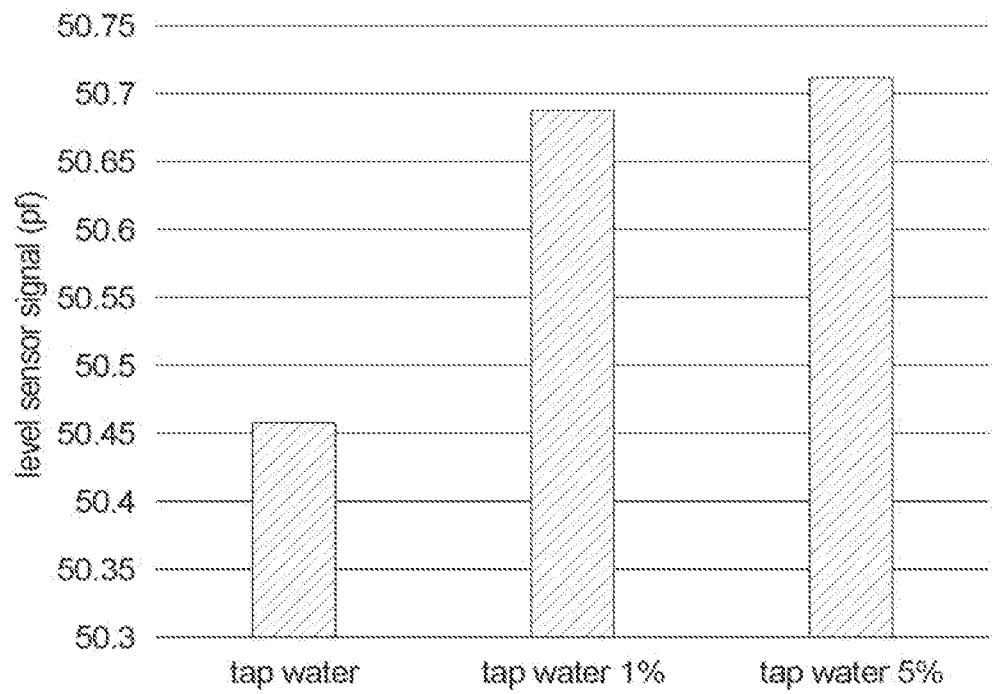
FIG. 18 is a plot illustrating outputs of a capacitance sensor of the present disclosure for water at different sodium (conductivity) levels.
Figure 19:
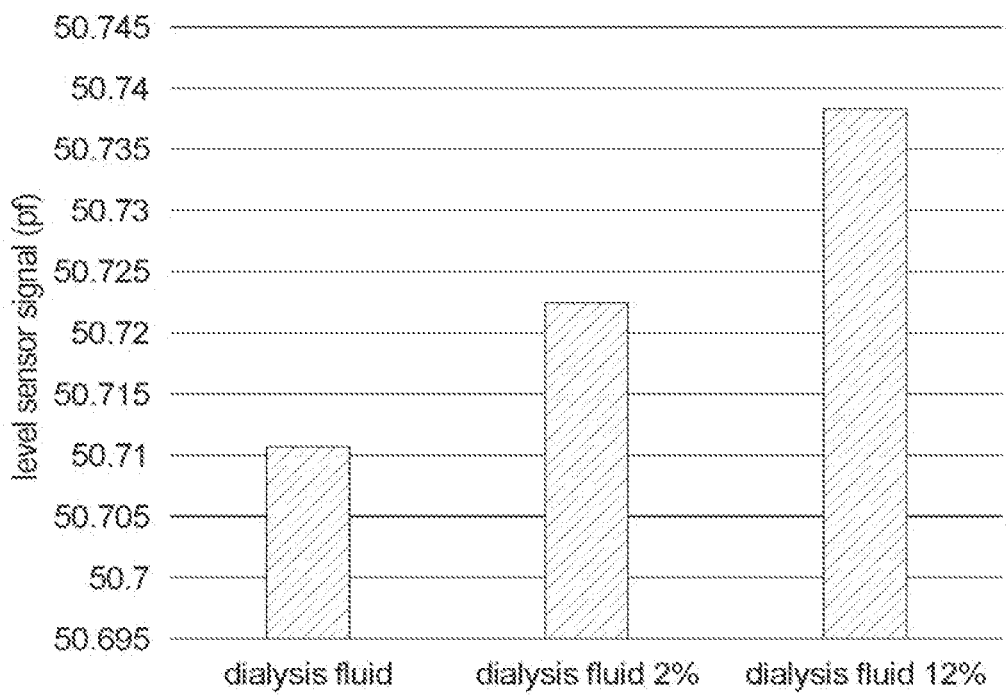
FIG. 19 is a plot illustrating outputs of a capacitance sensor of the present disclosure for dialysis fluid at different sodium (conductivity) levels.

It is known that there is a relationship between the conductivity and the dielectric of a fluid. Conductivity is used as a measure to determine the effectiveness of a peritoneal dialysis treatment. FIGS. 18 and 19 are plots of the outputs of the capacitance sensors of the present disclosure having capacitive sensing plates or electrodes 44a and 44b and 46a and 46b and associated capacitance sensor circuits 60 versus water (FIG. 18) and dialysis fluid (FIG. 19) at different sodium (conductivity) levels. Conductivity clearly has an effect the output of the capacitance sensors of the present disclosure.

It is accordingly contemplated to use an empirical model that relates a particular capacitance reading via 44a and 44b and/or 46a and 46b and associated capacitance sensor circuits 60 to a data point that is used to determine the effectiveness of a peritoneal dialysis treatment. The software employing the model may be installed at control unit of cycler 50, wherein the converted effectiveness data is sent to the doctor or clinician, or may be installed at the doctor or clinician computer, wherein the capacitance readings are sent to the doctor or clinician for conversion into effectiveness data.

One possible peritoneal effectiveness test procedure programmed on control unit 50 of system 10 causes first and second chambers 110a and 110b of manifold 110 or 210 to be filled with fresh dialysis fluid, after which a capacitance measurement $f_{fresh}$, is taken using capacitive sensing plates or electrodes 44a and 44b and/or 46a and 46b and associated capacitance sensor circuits 60. That fluid is drained after which control unit 50 cases both first and second chambers 110a and 110b of manifold 110 or 210 to be filled with patient effluent, after which a second capacitance measurement ($f_{effluent}$) is taken using capacitive sensing plates or electrodes 44a and 44b and/or 46a and 46b and associated capacitance sensor circuits 60. Control unit 50 then determines a difference between the two readings ($\Delta f = f_{fresh} - f_{effluent}$), records same in one or more memory 54 of APD cycler 20 and sends same via the network to the doctor's or clinician's computer for clinical analysis. Alternatively, control unit 50 converts $\Delta f$ into effectiveness data using the empirical model and sends the peritoneal dialysis effectiveness data via the network to the doctor's or clinician's computer for clinical analysis.

The peritoneal effectiveness evaluation is advantageous for at least three reasons. First, the evaluation may be performed on a regular basis, even per treatment or per patient drain if desired, without having to make the patient travel to have a test performed. Second, the test is easy to perform such that it does not unduly interrupt treatment. Third, the capacitance measurement is non-invasive, that is, it does not require a probe or electrode to contact the fluid being sensed as is the case with typical conductivity sensors. Sterility and cost issues with such contact are thus avoided.

It should be understood that various changes and modifications to the presently preferred embodiments described herein will be apparent to those skilled in the art. It is therefore intended that such changes and modifications be covered by the appended claims. For example, while the embodiments described herein set forth two capacitance sensors (two pairs of capacitive sensing plates or electrodes), a single capacitance sensor (one pair of capacitive sensing plates or electrodes) may be provided instead. In another example, while the capacitance sensors have been described herein operating with a two or three chamber rigid manifold, the capacitance sensors may operate alternatively with a single chamber rigid manifold. In a further example, while the valves have been described herein as pinch valves, other types of valves may be used alternatively, e.g., volcano valves provided with rigid plastic manifold 110, 210, 310, 410 and 510. Moreover, while the calibration sequences or routines discussed herein apply to peristaltic pump actuation, use of the capacitance sensors of the present disclosure to look for air to purge may be used with any type of dialysis fluid pumping, e.g., membrane, volumetric, piston, etc.

The invention is claimed as follows:

1. A peritoneal dialysis ("PD") system comprising:
   a cycler including
      an actuation surface having a peristaltic pump actuator, and
      a pair of capacitive sensing plates;
   a manifold assembly including
      a rigid manifold having first, second and third chambers, the rigid manifold configured and arranged to be abutted against the actuation surface for operation, wherein the pair of capacitive sensing plates is positioned to be operable with the first chamber, and
      a peristaltic pump tube extending from the first chamber to the second chamber of the rigid manifold; and
   a control unit configured to (i) cause the peristaltic pump actuator to actuate the peristaltic pump tube at a known revolutions per minute ("rpm") to empty dialysis fluid from the first chamber to the second chamber, wherein air backfills the first chamber from the third chamber, (ii) receive a signal from the pair of capacitive sensing plates indicating that the first chamber is empty, (iii) record a time duration $\Delta t$ needed to empty the dialysis fluid from the first chamber to the second chamber, (iv) determine a current volume per revolution for the peristaltic pump actuator by performing a first division of a known volume of the first chamber by the time duration $\Delta t$ and a second division of a result of the first division by the known rpm, and (v) use the current volume per revolution for at least one subsequent operation of the peristaltic pump actuator.

2. The PD system of claim 1, wherein the control unit is configured to use the signal from the pair of capacitive sensing plates to confirm that the first chamber is full of the dialysis fluid prior to performing the (i).

3. The PD system of claim 1, wherein the current volume per revolution is for a first direction of the peristaltic pump actuator, and wherein the control unit is further configured to (vi) cause the peristaltic pump actuator to actuate the peristaltic pump tube at a known revolutions per minute ("rpm") in a second direction to fill the first chamber with the dialysis fluid from the second chamber, wherein the third chamber accepts the air displaced from the first chamber, (vii) receive a signal from the pair of capacitive sensing plates indicating that the first chamber is full, (viii) record a time duration $\Delta t$ needed to fill the dialysis fluid from the second chamber to the first chamber, (ix) determine a current volume per revolution for the peristaltic pump actuator in the second direction by performing a third division of the known volume of the first chamber by the time duration $\Delta t$ needed to fill the dialysis fluid from the second chamber to the first chamber and a fourth division of a result of the third division by the known rpm in the second direction, and (x) use the current volume per revolution in the second direction for an additional at least one subsequent operation of the peristaltic pump actuator.

4. The PD system of claim 3, wherein the first direction is a patient fill direction and the second direction is a patient drain direction.

5. The PD system of claim 3, wherein the control unit is configured to repeat the (i) to the (v) and/or the (vi) to the (x) in each of a plurality of cycles of a PD treatment.

6. The PD system of claim 1, wherein the cycler includes a door that encloses the rigid manifold after the rigid manifold is abutted against the actuation surface for the operation, the actuation surface containing one of the plates of the pair of capacitive sensing plates, and the door containing the other plate of the pair of capacitive sensing plates.

7. The PD system of claim 6, wherein the one of the plates of the pair of capacitive sensing plates contained by the actuation surface is parallel to and directly opposes the other plate of the pair of capacitive sensing plates contained by the door.

8. The PD system of claim 1, wherein the use of the current volume per revolution for the at least one subsequent operation of the peristaltic pump actuator includes multiplying the current volume per revolution by a number of revolutions recorded by the control unit during each of the at least one subsequent operation.

9. The PD system of claim 8, wherein the number of revolutions takes into account a fraction of a revolution.

* * * * *